United States Patent
Reilly et al.

(10) Patent No.: US 7,025,757 B2
(45) Date of Patent: Apr. 11, 2006

(54) SYRINGE LOADING DEVICES FOR USE WITH SYRINGES AND MEDICAL INJECTORS

(75) Inventors: David M. Reilly, Glenshaw, PA (US); Frederick W. Trombley, III, Gibsonia, PA (US); Mark Trocki, Cheswick, PA (US)

(73) Assignee: Medrad, Inc., Indianola, PA (US)

( * ) Notice: Subject to any disclaimer, the term of this patent is extended or adjusted under 35 U.S.C. 154(b) by 40 days.

(21) Appl. No.: 10/067,003

(22) Filed: Feb. 4, 2002

(65) Prior Publication Data

US 2002/0107481 A1    Aug. 8, 2002

Related U.S. Application Data

(60) Provisional application No. 60/317,605, filed on Sep. 6, 2001, provisional application No. 60/267,303, filed on Feb. 8, 2001.

(51) Int. Cl.
- A61M 31/00 (2006.01)
- A61M 3/315 (2006.01)
- A61M 5/30 (2006.01)

(52) U.S. Cl. .................. 604/506; 604/67; 604/218; 604/315; 604/71

(58) Field of Classification Search .............. 604/67, 604/135, 523, 71, 70, 97, 99–100, 51–65, 604/506, 154–150, 232, 209, 218, 315, 892.1, 604/152
See application file for complete search history.

(56) References Cited

U.S. PATENT DOCUMENTS

| | | | |
|---|---|---|---|
| 2,463,113 A | 3/1949 | Klein | |
| 2,821,193 A * | 1/1958 | Kish et al. | 604/71 |
| 3,517,668 A | 6/1970 | Brickson | |
| 4,006,736 A | 2/1977 | Kranys et al. | |
| 4,465,474 A * | 8/1984 | Mardorf et al. | 604/154 |
| 4,472,141 A | 9/1984 | Dragan | |
| 4,677,980 A | 7/1987 | Reilly et al. | |
| 4,681,566 A * | 7/1987 | Fenton et al. | 604/135 |
| 4,838,857 A * | 6/1989 | Strowe et al. | 604/67 |

(Continued)

FOREIGN PATENT DOCUMENTS

| | | |
|---|---|---|
| EP | 0 584 531 | 2/1994 |
| WO | WO 01/08727 | 2/2001 |
| WO | WO 02/070049 | 12/2002 |

OTHER PUBLICATIONS

Unsigned Letter to Gregory L. Bradley listing four (4) references (dated Jan. 9, 2003).

(Continued)

*Primary Examiner*—Nicholas D. Lucchesi
*Assistant Examiner*—Roz Maiorino
(74) *Attorney, Agent, or Firm*—Gregory L. Bradley; Christian E. Schuster

(57) ABSTRACT

A syringe loading/filling device (or "syringe loader") includes a syringe mounting mechanism adapted to cooperate with an attachment mechanism of a syringe to attach the syringe to the syringe loader and a drive member adapted to impart motion to the syringe plunger. The syringes for use with the syringe loader include a syringe plunger slidably disposed therein and an attachment mechanism for attachment of the syringe to an injector. Such injectors include a mounting mechanism adapted to cooperate with the attachment mechanism on the syringe to mount the syringe on the injector.

6 Claims, 23 Drawing Sheets

U.S. PATENT DOCUMENTS

| | | | |
|---|---|---|---|
| 5,322,511 A * | 6/1994 | Armbruster et al. | 604/155 |
| 5,383,858 A * | 1/1995 | Reilly et al. | 604/152 |
| 5,507,727 A * | 4/1996 | Crainich | 604/97.02 |
| 5,520,653 A | 5/1996 | Reilly et al. | |
| 5,830,194 A * | 11/1998 | Anwar et al. | 604/223 |
| 6,048,334 A * | 4/2000 | Hirschman et al. | 604/154 |
| 6,068,164 A | 5/2000 | Totaro | |
| 6,090,064 A * | 7/2000 | Reilly et al. | 604/506 |
| 6,569,127 B1 * | 5/2003 | Fago et al. | 604/218 |
| 2001/0047153 A1 | 11/2001 | Trocki et al. | |
| 2003/0045789 A1 | 3/2003 | Thompson et al. | |

OTHER PUBLICATIONS

MCT & MCT Plus Front Load Injector Operation Manual, KMP 810PF, pp. 1-1 to 1-3, 2-1, 4-22 and 6-1 to 6-11 (1993).

EFD Syringe Filling Stations, web pages, www.efd-inc.com, EFD, Inc., East Providence, RI 02914 (1998-2002).

I & J Fisnar Automatic Barrell Loaders, web pages, www.ijfisnar.com, (no date).

Oxford Compounding Products, web pages, www.nutrinox.com, Oxford Nutrition, (no date).

International Search Report for Counterpart PCT Application No. PCT/US02/03210.

* cited by examiner

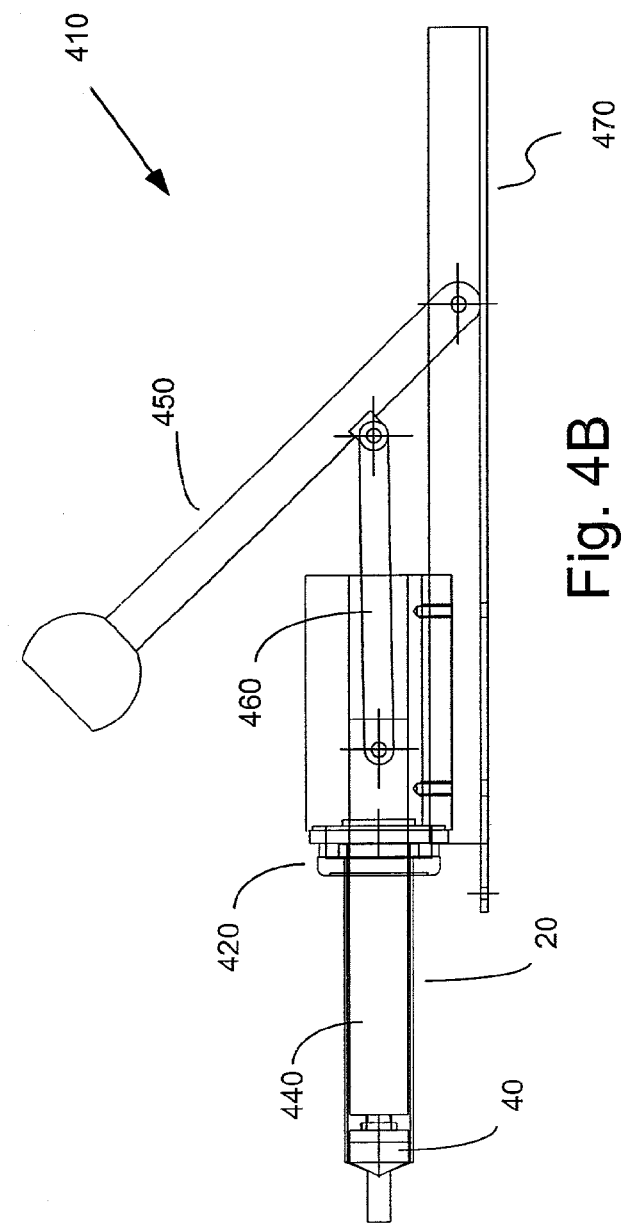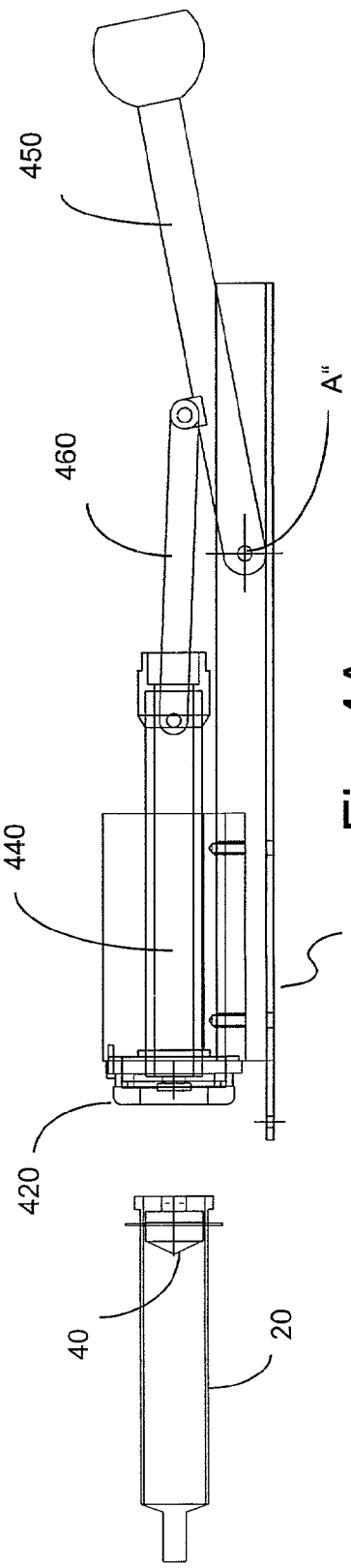
Fig. 4B
Fig. 4A

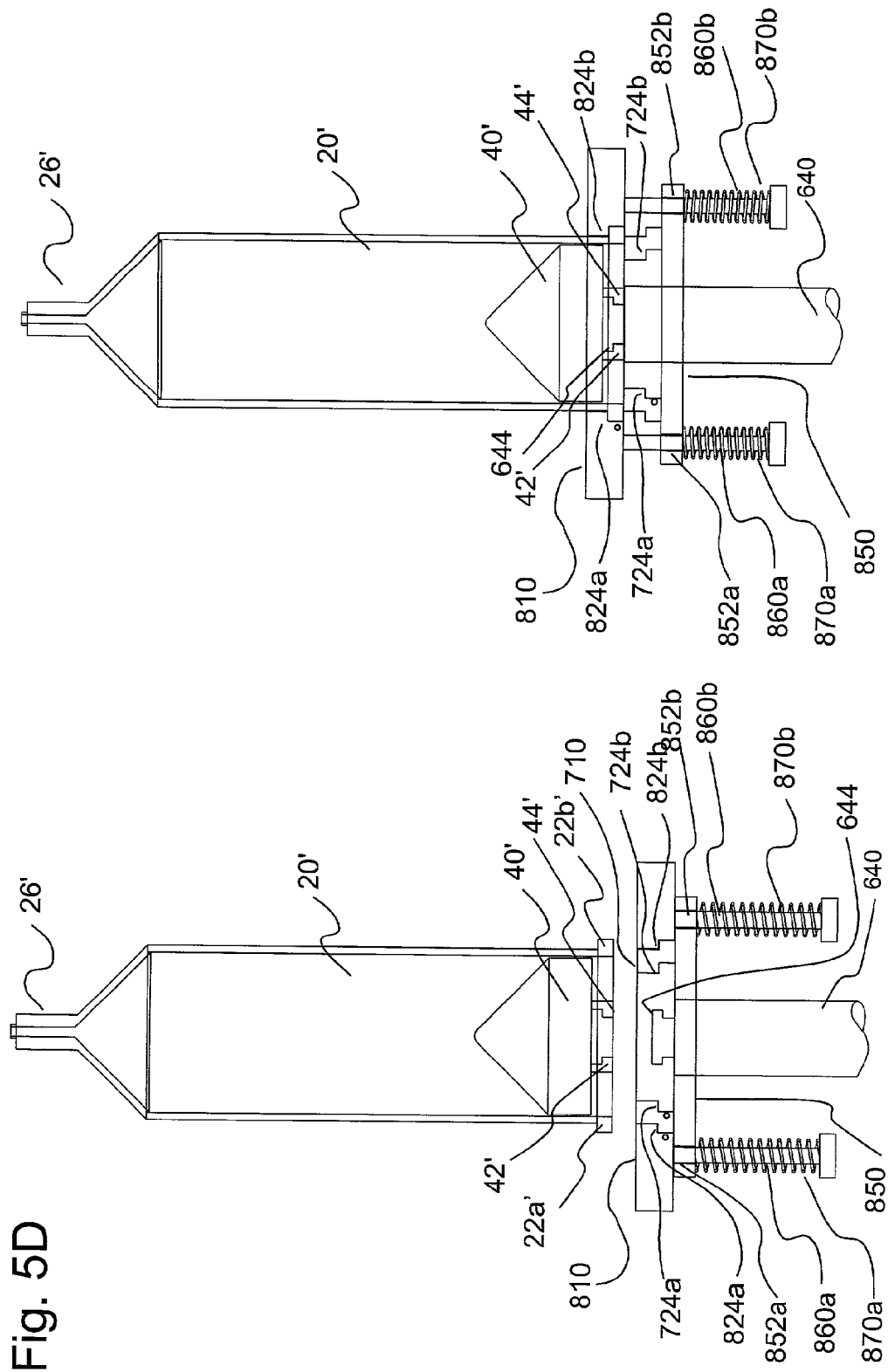

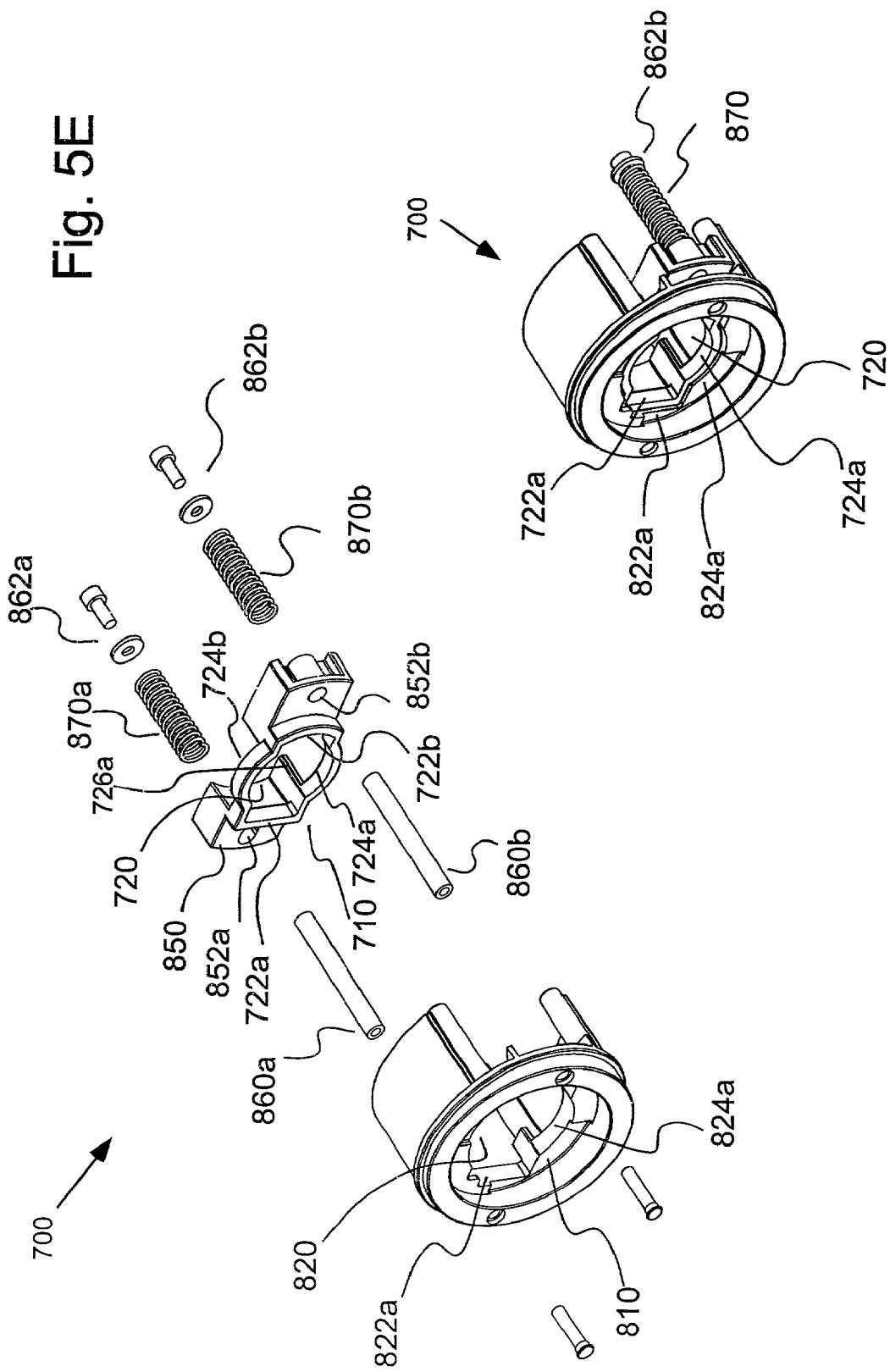

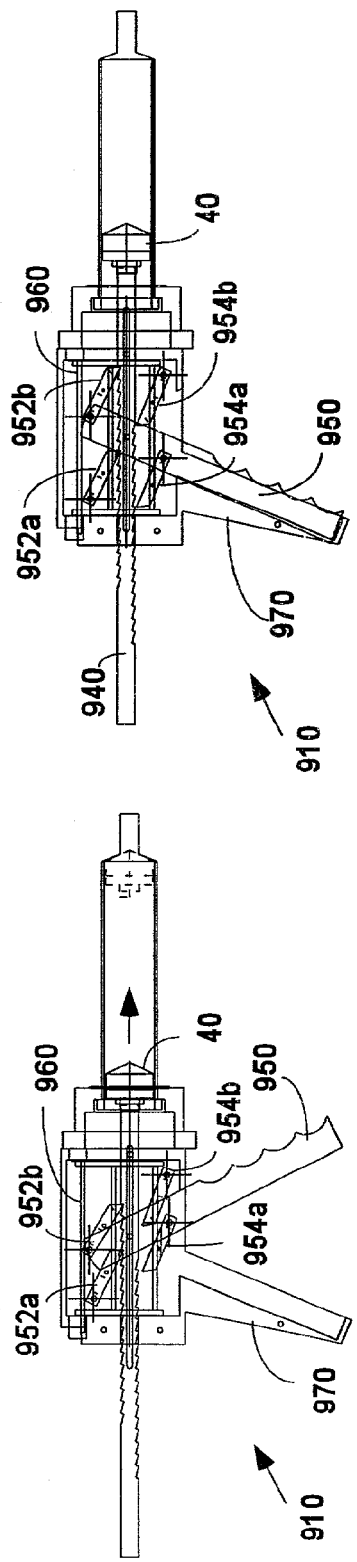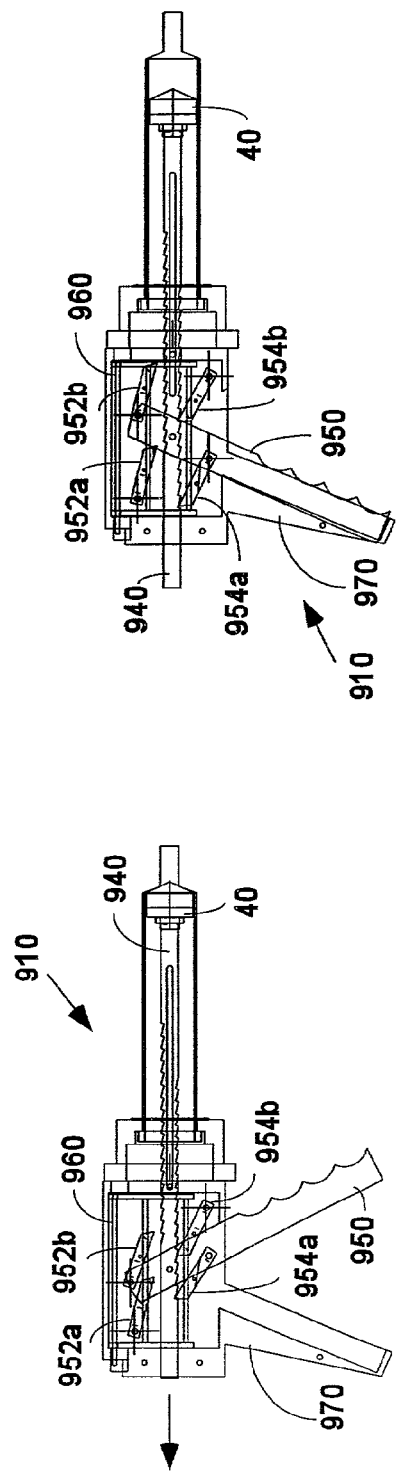
Fig. 6B

SYRINGE LOADING DEVICES FOR USE WITH SYRINGES AND MEDICAL INJECTORS

CROSS-REFERENCE TO RELATED APPLICATIONS

This application claims the benefit of Provisional Application No. 60/317,605, filed on Sep. 6, 2001, and Provisional Application No. 60/267,303, filed on Feb. 8, 2001, the contents of which are hereby incorporated by reference.

BACKGROUND OF THE INVENTION

The present invention relates to syringes and syringe loading devices and, more particularly, to syringes, syringe loading devices and medical injectors and to medical injector systems including such syringes and syringe loading devices.

A number of injector-actuated syringes and powered injectors for use in medical procedures such as angiography, computed tomography, ultrasound and magnetic resonance imaging (MRI) have been developed. U.S. Pat. No. 4,006, 736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

The front-loading injector of U.S. Pat. No. 5,383,858 includes a releasable mounting mechanism for securing the syringe to the front wall of the injector. Other types of releasable mounting mechanisms for front-loading syringes are disclosed in U.S. Patent Application Publication No. 2001-0047153, assigned to the assignee of the present invention, the disclosure of which is incorporated herein by reference The use of specifically designed mounting mechanisms generally limits the use of syringes of other various types with front-loading injectors. Syringe adapters attachable to those front-loading injectors are sometimes used to allow the use of such syringes with the front-loading injectors. For example, U.S. Pat. No. 5,520,653 discloses several adapters designed to allow the use of various syringes with a front-loading injector. Other adapters for front-loading injectors are disclosed, for example, in PCT Publication No. WO 01/08727 and U.S. patent application Ser. No. 09/633,299, filed on Aug. 8, 2000, each assigned to the assignee of the present invention, the disclosures of which are incorporated herein by reference.

Syringes are typically purchased either in a "prefilled" state, containing injection fluid supplied by the manufacturer, or in an empty, "fillable" state. Under current practice, empty syringes are typically attached to or loaded onto the power injector (either directly or via an adapter as known in the art) and connected to a source of injection fluid via, for example, tubing. The drive member of the powered injector is then reversed to draw the syringe plunger rearward within the syringe, thereby drawing injection fluid into the syringe for later injection into a patient. In many medical applications, however, powered injectors are used in procedures and areas in which there are substantial time and access constraints. For example, such time and access constraints often occur in MRI. In an MR suite, space is inherently limited. Injector access is limited as a result of such space limitation and lengthy scan times for patients. In time and/or access constrained procedures, loading of injection fluid into empty syringes using a powered injector results in inefficient use of personnel, equipment, time and/or space.

It is, therefore, very desirable to develop improved syringe loading/filling devices, and systems and methods to improve the efficiency of use of personnel, equipment, time and/or space.

SUMMARY OF THE INVENTION

In one aspect, the present invention provides a syringe loading device (or "syringe loader") for loading an injection fluid into a syringe. The syringes for use with the syringe loader include a syringe plunger slidably disposed therein and an attachment mechanism for attachment of the syringe to an injector. The injector includes a mounting mechanism adapted to cooperate with the attachment mechanism on the syringe to mount the syringe on the injector. The syringe loader includes generally a syringe mounting mechanism adapted to cooperate with the attachment mechanism of the syringe to attach the syringe to the syringe loader and a drive member adapted to impart motion to the syringe plunger.

In one embodiment, the drive member includes a flange on a rearward end thereof that is manually operated by a user during loading. In another embodiment, the drive member is linked to a lever arm, which is rotatable to impart reciprocal linear motion to the syringe plunger. An axis of rotation about which the lever arm rotates can be fixed or movable (for example, to adjust the stroke thereof). In a further embodiment, the drive member is powered (for example, via connection with or integration with a powered screw drive). Virtually any type of power source (for example, electric, hydraulic, pneumatic, etc.) can be used.

In still a further embodiment, the drive member includes one or more ratchet teeth. The syringe loader in this embodiment includes a rotating handle that is rotatable about an axis. The rotating handle has attached thereto on a first side of the axis a first pawl and on a second side of the axis a second pawl. The syringe loader also includes a mechanism to bring only one of the first pawl and the second pawl into cooperation with the ratchet teeth of the drive member at a given time. Rotation of the handle in a first direction causes forward movement of the drive member when the first pawl is brought into cooperation with the ratchet teeth. Rotation of the handle in the first direction causes rearward movement of the drive member with the second pawl is brought into cooperation with the ratchet teeth. The rotating handle is preferably biased in a second, "open" direction, opposite of the first direction.

In another aspect, the present invention provides a syringe loader for loading an injection fluid into a syringe including a syringe tip from which pressurized injection fluid exits the syringe during an injection procedure. The syringe loader includes a connector to connect a source of injection fluid to the syringe tip. The connector includes a first connection mechanism to connect to the syringe tip and a second connection mechanism to connect to the source of injection fluid. The connector further includes a valve to open and close the fluid connection between the source of injection fluid and the syringe tip. The connector also includes an inlet between the valve and the second connection mechanism that is adapted to pass a pressurized gas into the source of injection medium when the valve is closed. The valve is preferably openable after pressurized gas is passed into the source of injection fluid so that injection fluid is forced into the syringe via the syringe tip by the pressurized gas within the source of contrast fluid. In one embodiment, the syringe loader includes an air pump in fluid connection with the inlet to pass pressurized air into the source of injection fluid. The air pump can, for example, include a ball pump in fluid connection with a bladder.

In another aspect, the present invention provides a system including a syringe, an injector (preferably a powered injector) to pressurize an injection fluid loaded into the syringe, and a syringe loader to load the injection fluid into the syringe. The syringe loader is preferably operable independent of the injector. However, in an alternate embodiment, the operation of the syringe loader and the injector can be coordinated and/or interdependent, by means, for example, of a common control unit.

In a further aspect, the present invention provides a syringe loader for loading an injection fluid into a syringe independent of an injector. The syringe includes a syringe plunger slidably disposed therein and an attachment mechanism for attachment of the syringe to the injector, as described above. Likewise, the injector includes a mounting mechanism to cooperate with the attachment mechanism on the syringe to mount the syringe on the injector. The syringe loader includes a syringe mounting mechanism adapted to cooperate with the attachment mechanism of the syringe to attach the syringe to the syringe loader and a drive member to impart motion to the syringe plunger.

In one embodiment, the drive member of the syringe loader is in operative connection with a manual lever arm. The lever arm can, for example, be in operative connection with the drive member via a linkage assembly. In one embodiment, the syringe loader includes a support frame having a first slot therein. In this embodiment, the lever arm can be rotatably connected to the drive member via a first pin positioned intermediate between the forward end and the rearward end of the lever arm. The first pin travels in the first slot during rotation of the lever arm. The support frame can further include a second slot formed therein. The lever arm in this embodiment has a second pin attached thereto at a position forward of the position of the first pin. The second pin travels in the second slot during rotation of the lever arm.

The syringe loader can also include a mount that is attachable to a surface, such as a wall or a table. Preferably, the support frame is removably attachable to the mount.

In still another aspect, the present invention provides a method of injecting a fluid into a patient using a syringe in which an injection fluid loaded into the syringe is pressurized by an injector. The method includes the step of loading the injection fluid into the syringe using a syringe loader that is operable independent of the powered injector.

The method can further include the step of mounting the syringe loader on a surface prior to loading the injection fluid. For example, the syringe loader can be mounted on a wall. The method further includes the steps of attaching the syringe to the syringe loader prior to loading the injection fluid into the syringe and removing the syringe from the syringe loader after loading of the syringe. The syringe can be attached to the syringe loader in generally the same manner in which the syringe is attached to the injector.

The syringe loading/filling devices, systems and methods of the present invention improve the efficiency of use of personnel, equipment, time and/or space in injection procedures as compared to current practices. Moreover, the syringe loading/filling devices, systems and methods of the present invention are relatively inexpensive to manufacture and implement. Furthermore, spills or leaks of injection fluid often occur during loading of injection fluid. Such spills or leaks of injection fluid can be very harmful to powered injectors if the injection fluid passes into the injector housing. The syringe loading/filling devices, systems and methods of the present invention assist in preventing damage to injectors from such spills or leaks.

Moreover, the syringe loaders of the present invention are readily made suitable for use in or near an MR environment. In that regard, the materials and operation of the syringe loaders of the present invention preferably do not substantially interfere with MRI equipment, and preferably the syringe loader does not experience excessive forces as a result of the relatively strong magnetic fields generated in an MR environment. In general, polymeric materials and non-ferrous metals (for example, aluminum or TEFLON® impregnated aluminum) are preferred construction materials for use in the syringe loaders of the present invention when such syringe loaders are to be used in or near an MR environment. Nonferrous metals and/or polymeric materials that are, for example, lubricious, low friction and/or "non-stick" can be used in the syringe mounts or interfaces of the syringe loaders of the present invention. Examples of suitable polymeric materials include polycarbonate and DELIN® available from E.I. duPont de Nemours & Co. of Wilmington, Del.

BRIEF DESCRIPTION OF THE DRAWINGS

Other aspects of the invention and their advantages will be discerned from the following detailed description when read in connection with the accompanying drawings, in which:

FIG. 4A illustrates a side, cross-sectional view of a second embodiment of a syringe loader of the present invention with the plunger extension thereof in a rearward or retracted position;

FIG. 4B illustrates a side, cross-sectional view of the syringe loader of FIG. 4A with the plunger extension thereof in a forward position;

FIG. 5D illustrates a top, cross-sectional view of an embodiment of a syringe interface of the syringe loader of FIG. 5A with a syringe of a second size connected thereto;

FIG. 5E illustrates a perspective view of the syringe interface of FIGS. 5C and 5D in an exploded or disassembled state and in an assembled state;

FIG. 5I illustrates top views of one embodiment of a process for using the syringe loader of FIG. 5A;

FIG. 6B illustrates side, cross-sectional views of the syringe loader of FIG. 6A during a fluid expelling cycle and a fluid loading cycle;

DETAILED DESCRIPTION OF THE INVENTION

The syringe loading devices (or "syringe loaders") of the present invention can be used in connection with a wide variety of syringes and injectors, including powered injectors. A couple of powered injectors and syringes in connection with which the syringe loader of the present invention can be used are described below.

Figure 1:
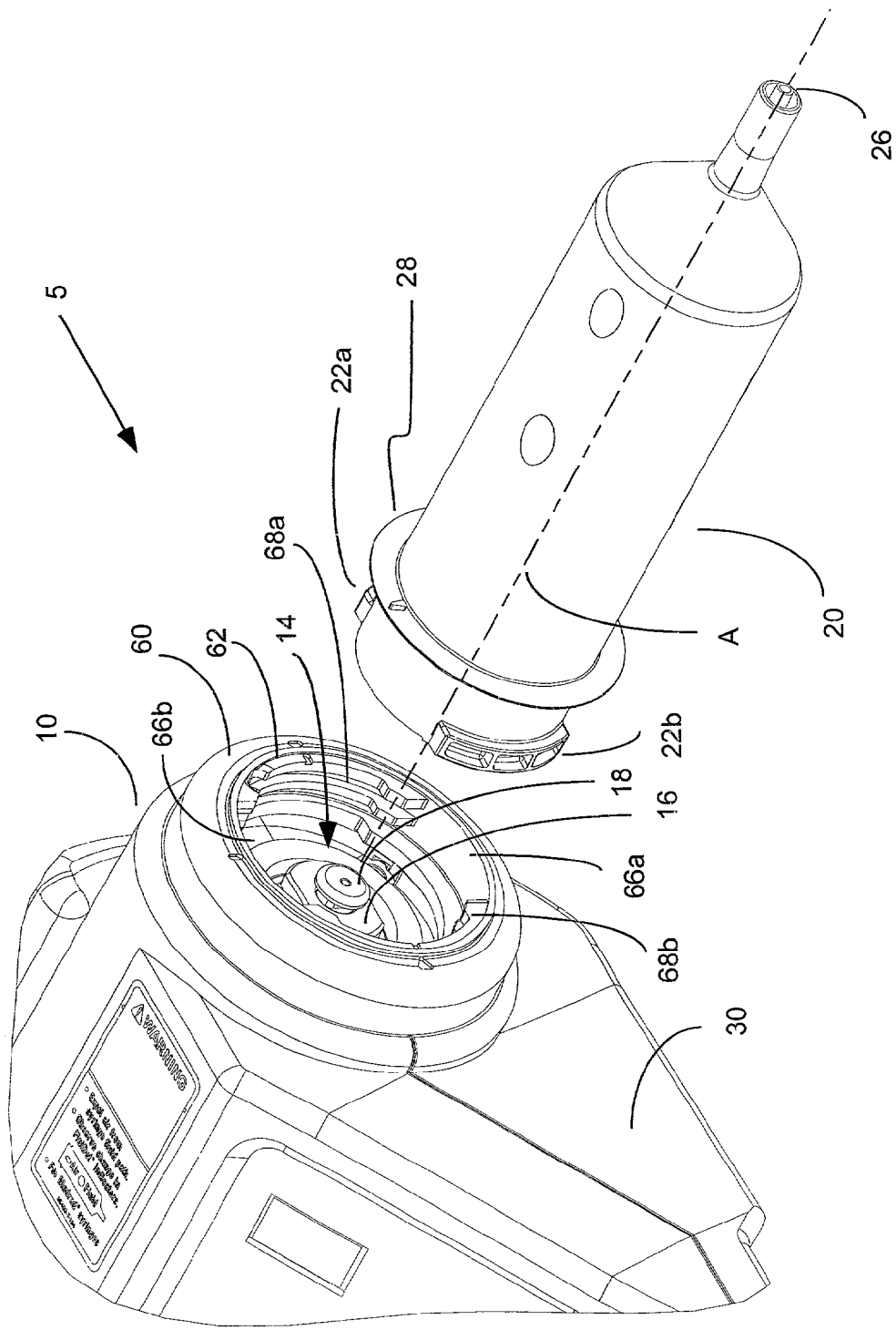
FIG. 1 illustrates a perspective view of an embodiment of an injector system including a powered injector and a front-loading syringe.

An embodiment of a front-loading injector system 5 is illustrated in FIG. 1. Injector system 5 includes a powered injector 10 and a syringe 20 for injection of, for example, a contrast medium. As illustrated in FIG. 1, injector housing 30 of injector 10 preferably includes a first drive member or piston 14 therein which cooperates with a syringe plunger 40 (not shown in FIG. 1; see, for example, FIG. 3E or 5C) slideably disposed in syringe 20 to inject a fluid from the interior of syringe 20 into a patient.

As used herein, the terms "axial" or "axially" refer generally to, for example, an axis A around which syringe 20 and piston 14 are preferably formed (although not necessarily symmetrically therearound) and to directions collinear with or parallel to such an axis. The terms "proximal" or "rearward" refer generally to an axial or a longitudinal direction toward the end of syringe 20 opposite a syringe tip 26 (from which pressurized fluid exits syringe 20). The terms "distal" or "forward" refer generally to an axial or a longitudinal direction toward the syringe tip 26 of syringe 20. The term "radial" refers generally to a direction normal to an axis such as axis A.

Syringe 20 is removably connected to injector 10 as described, for example, in U.S. Pat. No. 5,383,858, the disclosure of which is incorporated herein by reference. In that regard, front-loading injector 10 preferably includes a front portion or interface 60 having a first recess 62 formed therein. Piston or drive member 14 is reciprocally mounted within injector 10 and is extendible through recess 62. Piston 14 preferably includes a piston flange or head 16 to assist in forming a connection with the syringe plunger. Interface 60 includes receiving slots 66a and 66b, which are preferably positioned opposite one another around recess 62. Receiving flanges 68a and 68b are preferably positioned opposite one another and between receiving slots 66a and 66b, and extend inwardly into recess 62.

The rearward end of syringe 20 preferably includes a releasable mounting mechanism such as a pair of mounting flanges 22a and 22b for mounting syringe 20 in a desired position relative to the housing 30 of injector 10. Flange 22a is not well shown in FIG. 1 but is generally identical to flange 22b and positioned opposite flange 22b (see, for example, FIG. 5C).

To attach syringe 20 to injector 10, the rearward end of syringe 20 is inserted into injector recess 62 such that mounting flanges 22a and 22b are inserted into receiving slots 66a and 66b, respectively. In one embodiment, piston flange 16 is preferably simultaneously aligned to engage a capture mechanism (including, for example, L-shaped capture members 42 and 44—see, for example, FIG. 3E or 5C) on the rear of syringe plunger 40 (as, for example, described in U.S. Pat. No. 5,383,858). As clear to one skilled in the art, however, many other plunger and piston designs are possible to connect the piston 14 to the plunger 40.

Figure 3A:
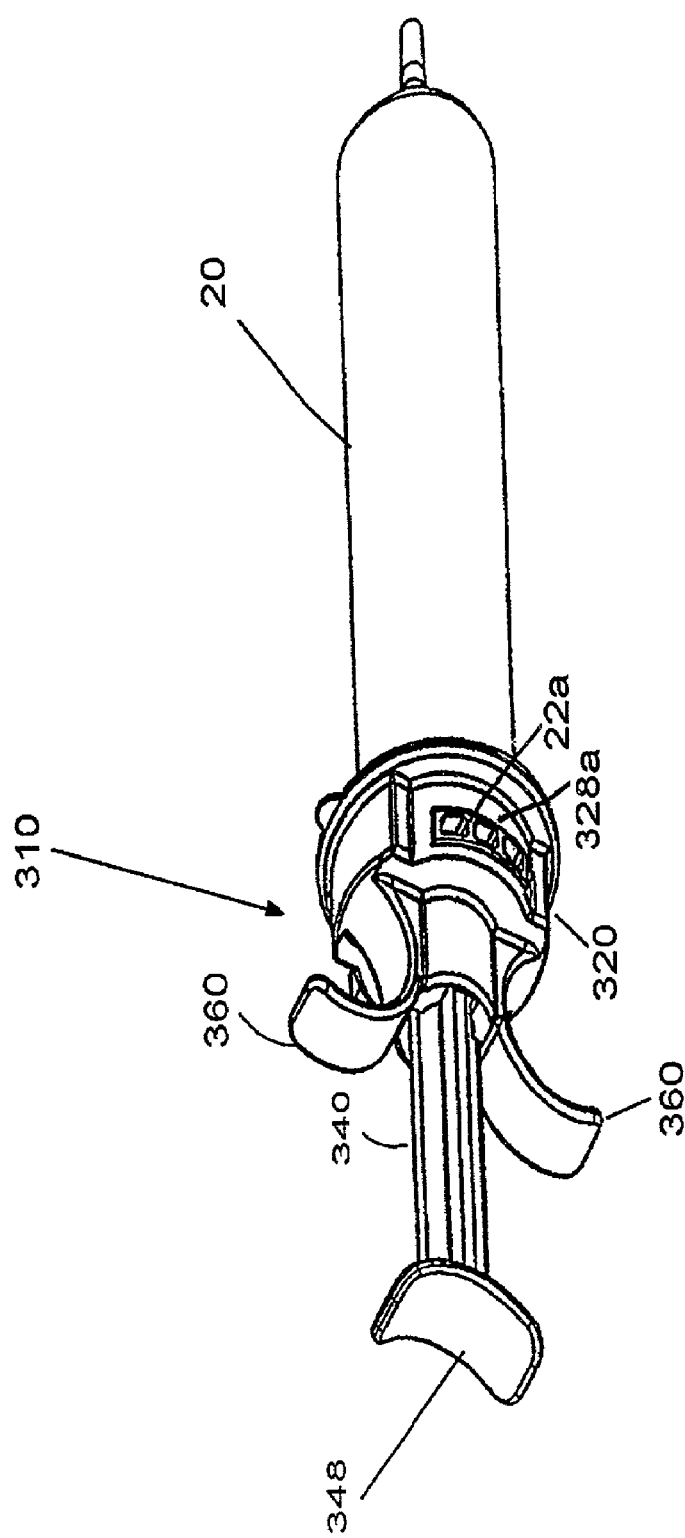
FIG. 3A illustrates a perspective view of a first embodiment of an off-injector syringe loader of the present invention in which the syringe loader is connected to the syringe.
Figure 3B:
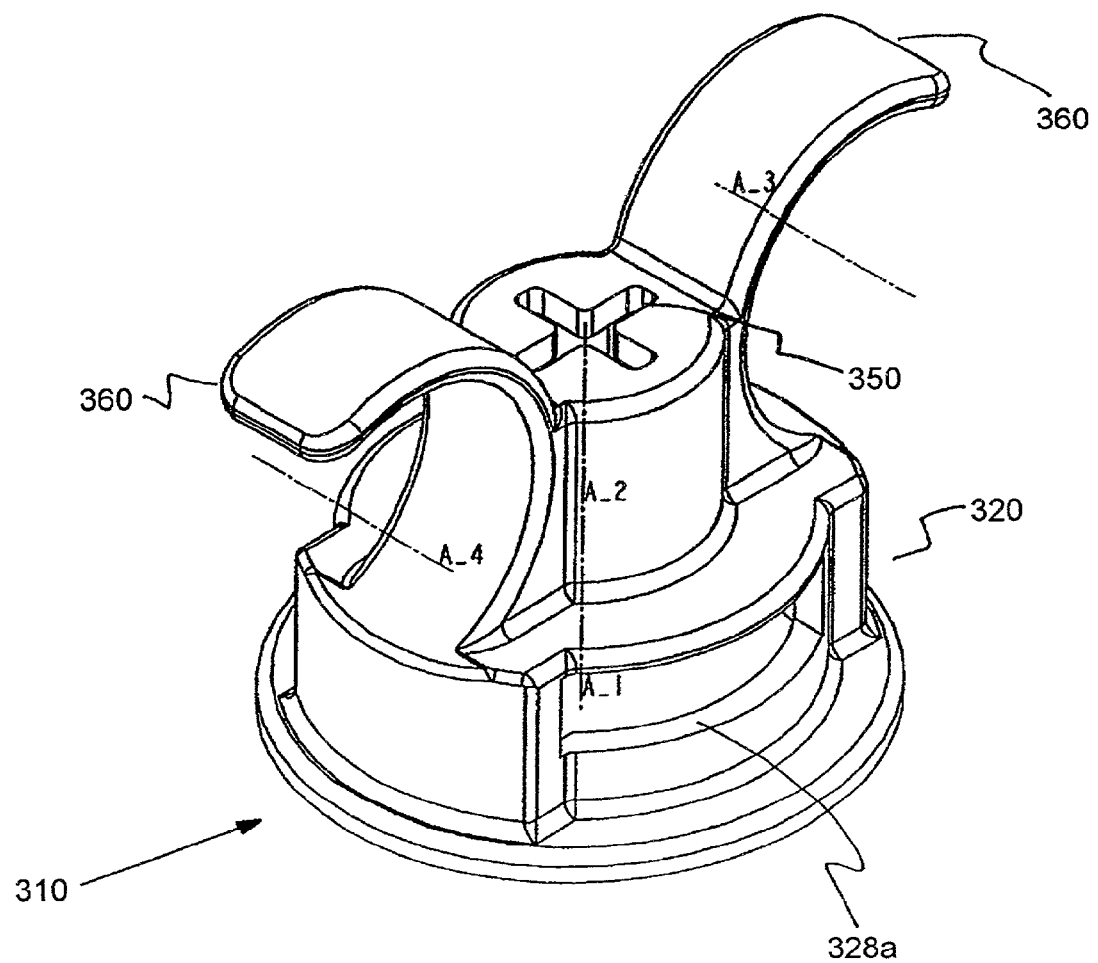
FIG. 3B illustrates a perspective view of the syringe loader of FIG. 3A in which the syringe has been disconnected from the loader.
Figure 3C:
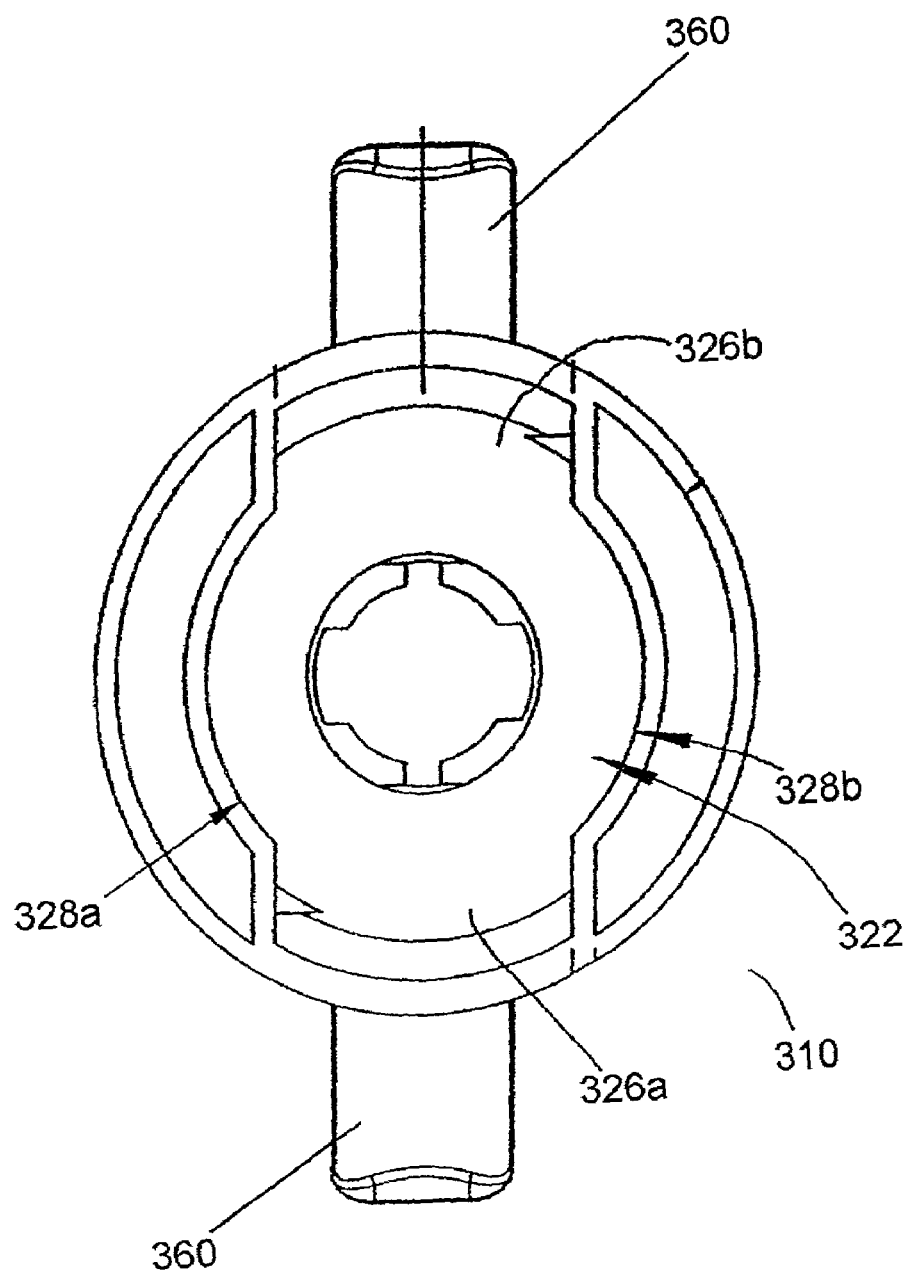
FIG. 3C illustrates a front view of the syringe loader of FIG. 3A.
Figure 3D:
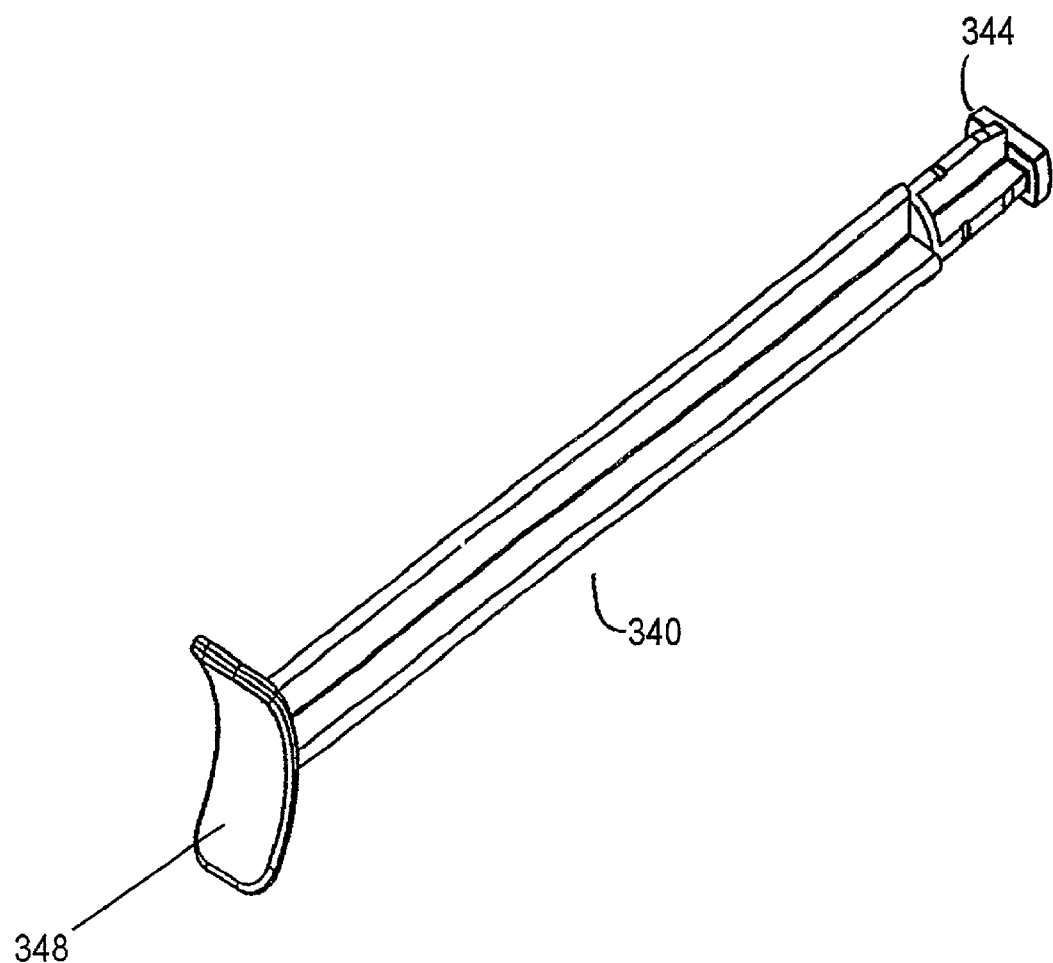
FIG. 3D illustrates a perspective view of the plunger extension of the syringe loader of FIG. 3A.
Figure 3E:
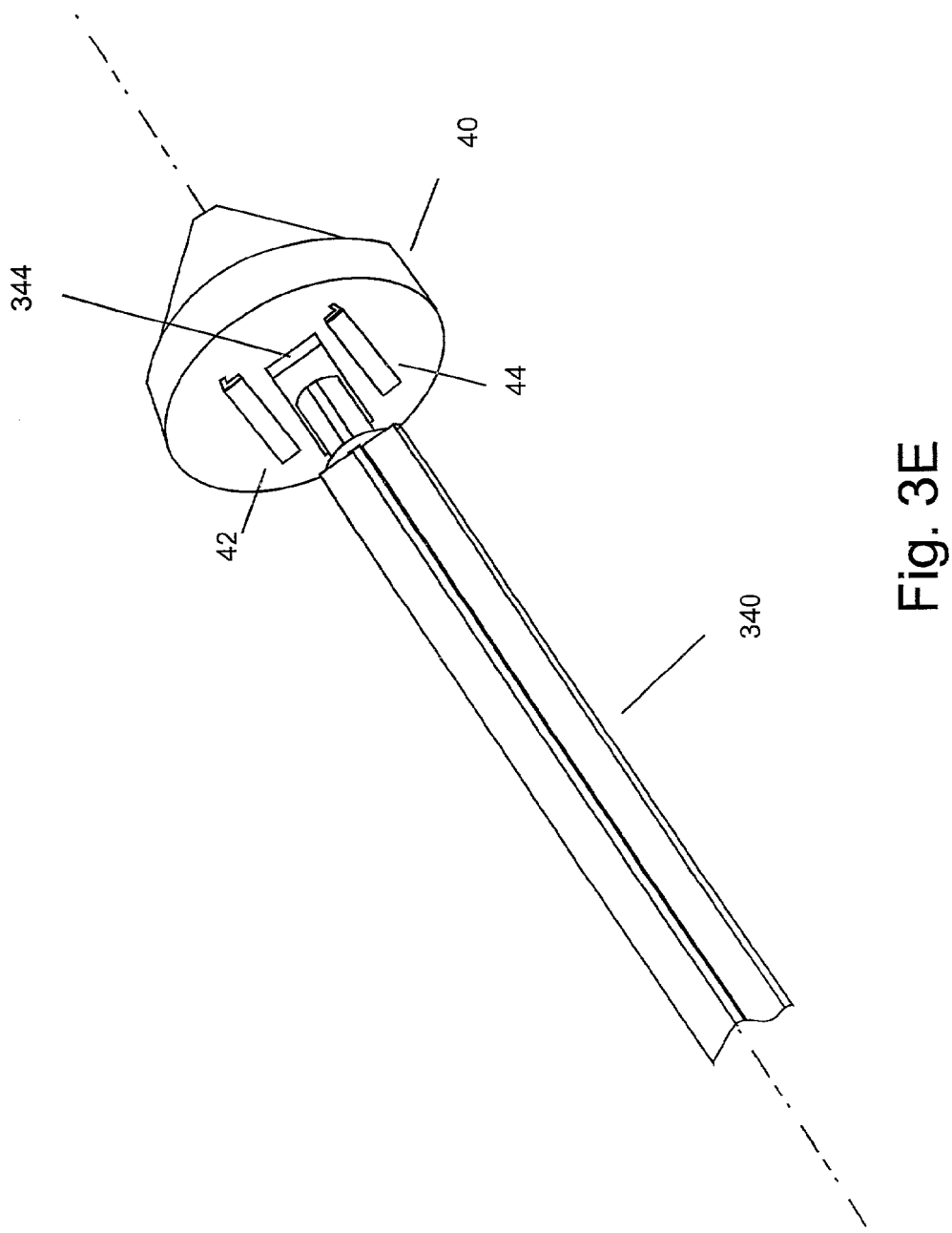
FIG. 3E illustrates a perspective view of the plunger extension of the syringe loader of FIG. 3A aligned with the syringe plunger.
Figure 5A:
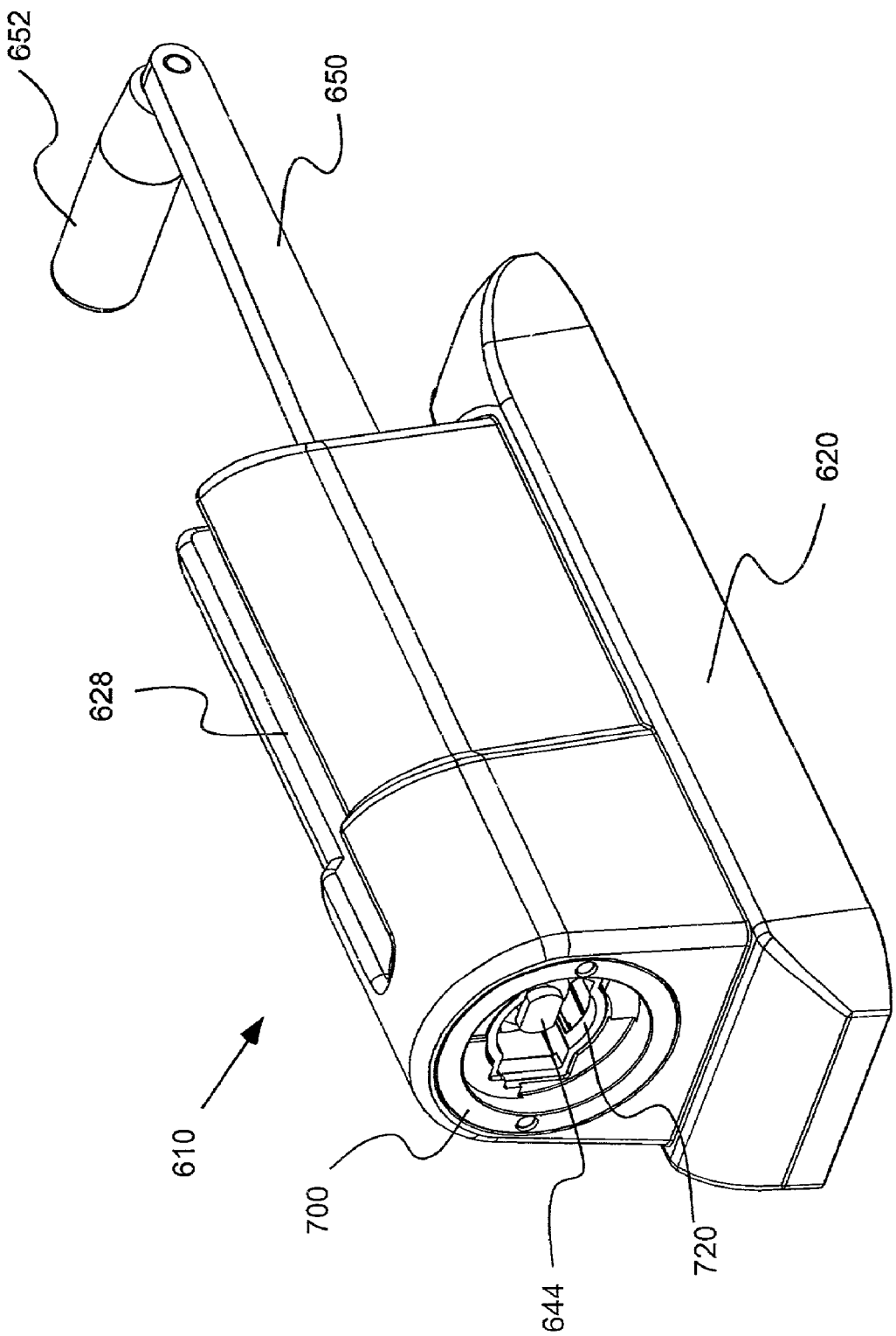
FIG. 5A illustrates a perspective view of another embodiment of a syringe loader of the present invention.
Figure 5B:
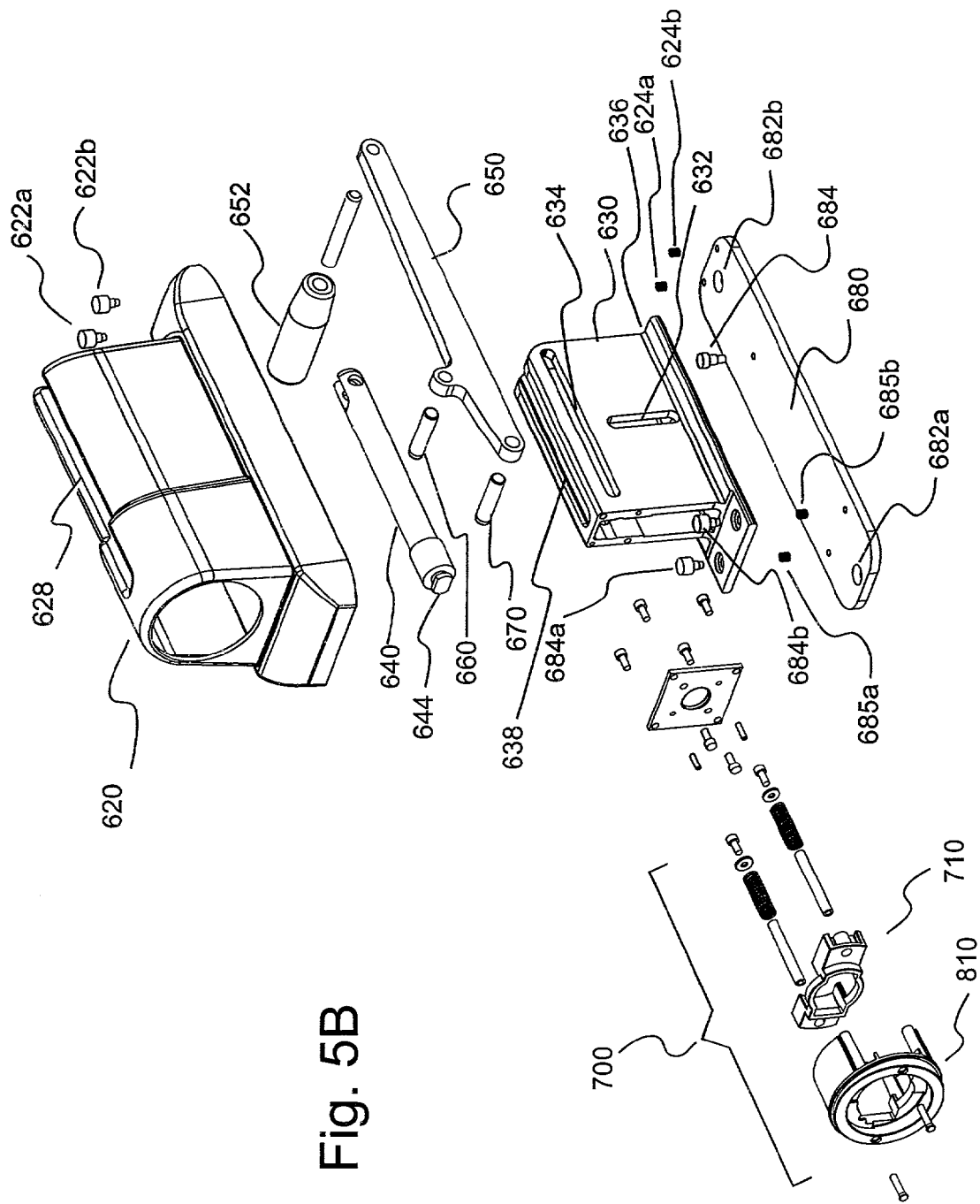
FIG. 5B illustrates a perspective, exploded or disassembled view of the syringe loader of FIG. 5A.
Figure 5C:
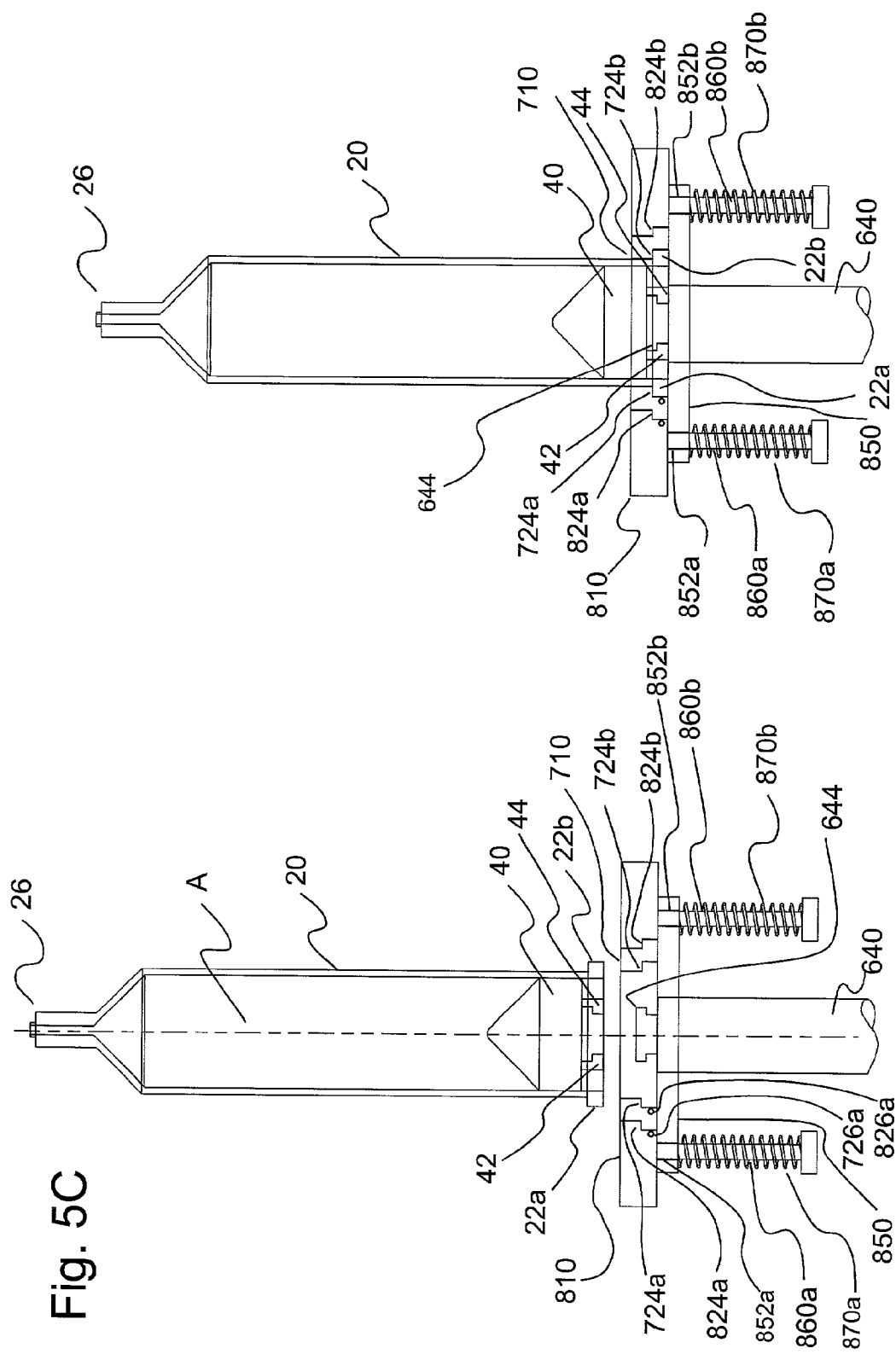
FIG. 5C illustrates a top, cross-sectional view of an embodiment of a syringe interface of the syringe loader of FIG. 5A with a syringe of a first size connected thereto.

Once mounting flanges 22a and 22b are inserted into receiving slots 66a and 66b, respectively, and piston 14 is in position to be received by plunger 40, the operator rotates syringe 20 approximately 90 degrees such that mounting flanges 22a and 22b move behind and are engaged by receiving flanges 68a and 68b, respectively, and piston flange 14 is retained by, for example, L-shaped capture members 42 and 44 on plunger 40 (see, for example, FIG. 3E or 5C). Injector 10 may include a stop mechanism (not shown), for example, extending from at least one of the retaining slots 68a and 68b, to prevent rotation of syringe 20 more than 90 degrees. Tactile, visual or audible feedback can be provided to the operator via, for example, cooperating members on syringe 20 and injector 10 to inform the operator that secure connection has been achieved. After securely attaching syringe 20 to injector 10, advancing piston 14 in a forward direction will apply a motive force to plunger 40 to advance plunger 40 forward within syringe 20, thereby forcing the contents of syringe 20 out of syringe tip 26 into the fluid path to the patient. Retracting piston 14 in a rearward direction will cause plunger 40 to move rearward within syringe 20, thereby drawing fluid into syringe 20.

Figure 2:
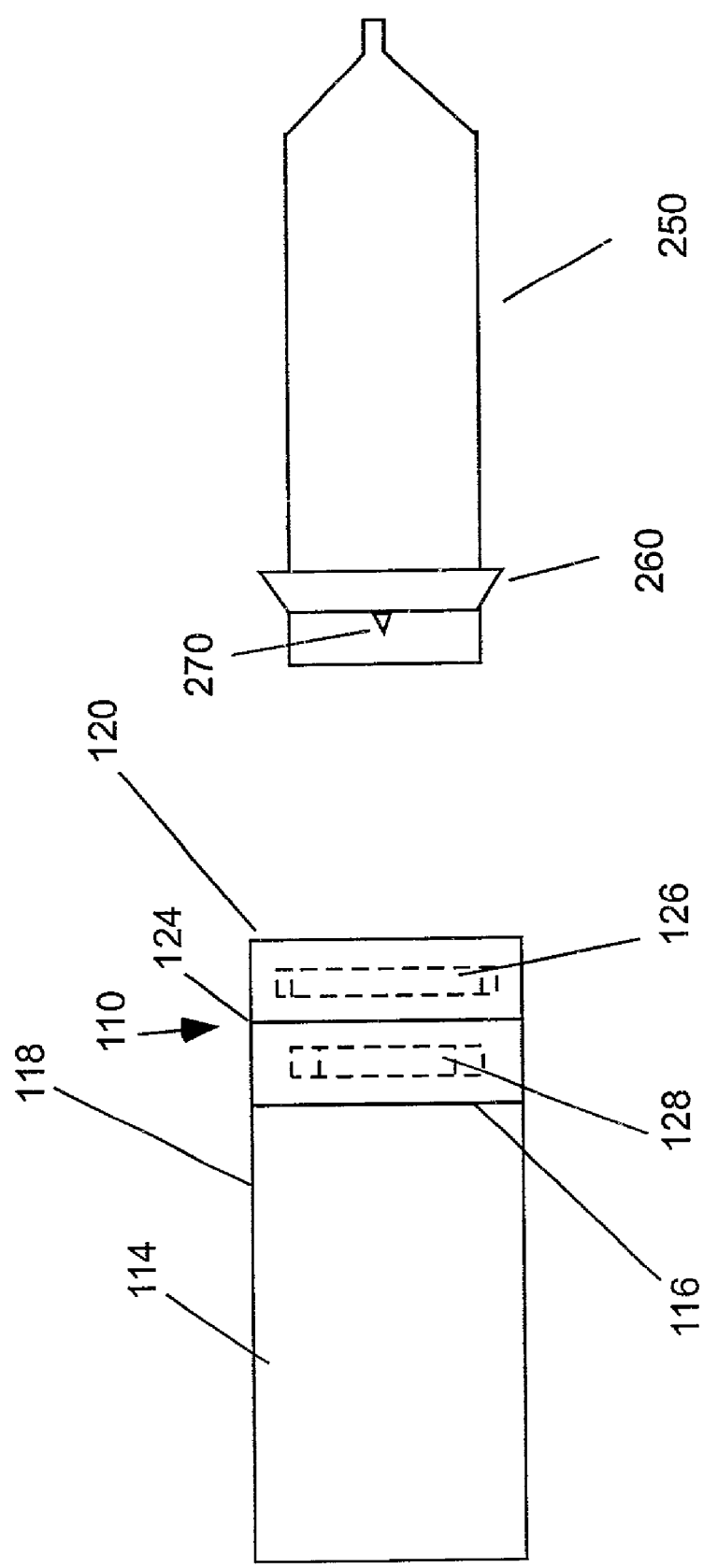
FIG. 2 illustrates a side view of another embodiment of a front-loading injector having a different releasable mounting mechanism.

As known in the art, syringes can be attached to a wide variety of front-loading injectors simply through modification of the rearward attachment mechanism of the syringe or through use of syringe adapters. In that regard, FIG. 2 illustrates another embodiment of an injector 114 and a syringe 250 having a different releasable mounting mechanism 110 than described above for injector 10. Release mechanism 110 includes a connector housing 124, which contains at least two elements that facilitate connection of syringe 250 to an injector 114. The first element is a flexible ring 126 disposed within release mechanism 110 near front end 120. The second element is a rotating ring 128 disposed within release mechanism 110 near rearward end 116. Flex ring 126 and rotating ring 128 cooperate with one another to permit connection and release of syringe 250 to and from release mechanism 110 (and, accordingly, to and from injector 114). Injector 114 and release mechanism 110 are described in detail in U.S. Patent Application Publication No. 2001-0047153, the contents of which are incorporated herein by reference.

In general flex ring 126 distends to an "open" shape when contacted by a sloped shoulder 260 on a rearward end of syringe 250 and then snaps back to a relaxed state once shoulder 260 passes thereby to retain syringe 250 within releasable mounting mechanism 110. After connection, rotation of syringe 250 about its axis (for example, approximately 90°) causes rotation of rotating ring 128 disposed within release mechanism 110 via cooperation of tab 270 with abutment members or grooves (not shown) on rotating ring 128. Rotation of ring 128 causes flex ring 126 to distend to its open shape to allow shoulder 260 to pass forward of flex ring 126 for removal of syringe 250 from releasable mounting mechanism 110.

Under current practice, powered injectors such as injector 10 or injector 114 are used to load or fill empty syringes with injection fluid (for example, a contrast medium). As discussed above, this methodology often results in inefficient use of equipment, personnel, time and/or space. FIGS. 3A–3E illustrate an embodiment of an off-injector, syringe loader 310 that can be used to load injection fluid into, for example, syringe 20 before syringe 20 is mounted upon injector 10. Syringe loader 310 includes a syringe mount 320 to removably attach syringe 20 thereto. In general, syringe 20 is connected to syringe mount 320 in the same way that syringe 20 is mounted to injector 10. In that regard, as best shown in FIG. 3B syringe mount 320 includes an opening 322 having receiving slots 326a and 326b positioned around the perimeter thereof. To attach syringe 20 to syringe mount 320 of loader 310, the rearward end of syringe 20 is inserted into opening 322 such that mounting flanges 22a and 22b are inserted into receiving slots 326a and 326b, respectively.

Once mounting flanges 22a and 22b are inserted into receiving slots 326a and 326b, respectively, the operator rotates syringe 20 approximately 90 degrees such that mounting flanges 22a and 22b move behind and are engaged by receiving flanges 328a and 328b, respectively. Tactile, visual or audible feedback can be provided to the operator as described above to inform the operator that secure connection has been achieved. After securely attaching syringe 20 to syringe loader 310, advancing a plunger extension or stem 340 in a forward direction will apply a motive force to the syringe plunger to advance the plunger forward within syringe 20, thereby expelling injection fluid from syringe tip 26. Likewise, retracting plunger extension 340 in a rearward direction will cause the plunger to move rearward within syringe 20, thereby drawing fluid into syringe 20. Syringe loader 310, when syringe 20 is connected thereto, thus operates similarly to a manual syringe and can be manually operated to load a desired amount of injection fluid into syringe 20. The loaded or filled syringe can then be mounted upon injector 10 as described above for injection of the fluid into a patient.

In one embodiment (see FIG. 3D), a flange 344 on a distal end of plunger extension 340 preferably engages a capture mechanism such as L-shaped capture members 42 and 44 on the rear of a syringe plunger 40 (see FIG. 3E; as, for example, described in U.S. Pat. No. 5,383,858). Preferably, this engagement occurs as syringe 20 is connected to loader 310. For example, plunger extension 340 is preferably in position to be received by plunger 40 when syringe 20 is inserted into opening 320. In that regard, syringe manufacturers typically ship syringes with the syringe plunger in a known position (for example, fully retracted). Loader 310 is preferably designed such that, for example, the fully retracted position of plunger extension 340 positions flange 344 to be received by plunger 40 when syringe 20 is fully inserted within opening 320.

When the operator rotates syringe 20 approximately 90 degrees such that mounting flanges 22a and 22b move behind and are engaged by receiving flanges 368a and 368b, respectively, flange 344 preferably rotates to engage L-shaped capture members 42 and 44. In this embodiment, plunger extension 340 is preferably slidably disposed within loader 310 such that plunger extension 340 cannot rotate about its axis relative to syringe mount 320 to ensure suitable alignment as described above. In the embodiment of FIGS. 3A through 3E, for example, plunger extension has a generally cross-shaped cross section which is slidably disposed within an correspondingly shaped opening 350 of loader 310 to prevent rotation of plunger extension 340 relative to the remainder of syringe loader 310.

Syringe loader 310 further includes finger grips 360 to facilitate manual operation thereof. Likewise, plunger extension 340 includes a rear flange 348 to facilitate manual operation of syringe loader 310.

FIGS. 4A and 4B illustrate another embodiment of an off-injector syringe loader 410 of the present invention. Syringe loader 410 includes a syringe mount 420 that operates generally in the manner of the mounting mechanism of interface 60 of injector 10 as well as syringe mount 320. A plunger extension 440, which imparts motion to plunger 40 as described above, is slidably disposed within the housing of syringe loader 410 to pass through a passage in syringe mount 420. Plunger extension 440 is in operative connection with a lever arm 450 via a linkage assembly arm 460. Lever arm 450 is rotatable about axis A" defined, for example, by a pin attached to a base member 470 to which syringe mount 420 is also preferably attached. Lever arm 450 provides mechanical advantage for ease of operation. Base 470 is preferably attachable to a surface (for example, a counter top or a wall) via any suitable attachment means (for example, screws). FIG. 4B illustrates rotation of lever arm 450 to a forward position to advance plunger 40 to a forward position within syringe 20. FIG. 4A illustrates rotation of lever arm 450 to a rearward position to allow syringe 20 to be mounted to syringe loader 410 (or to retract plunger 40 to a rearward position within syringe 20).

Figure 4C:
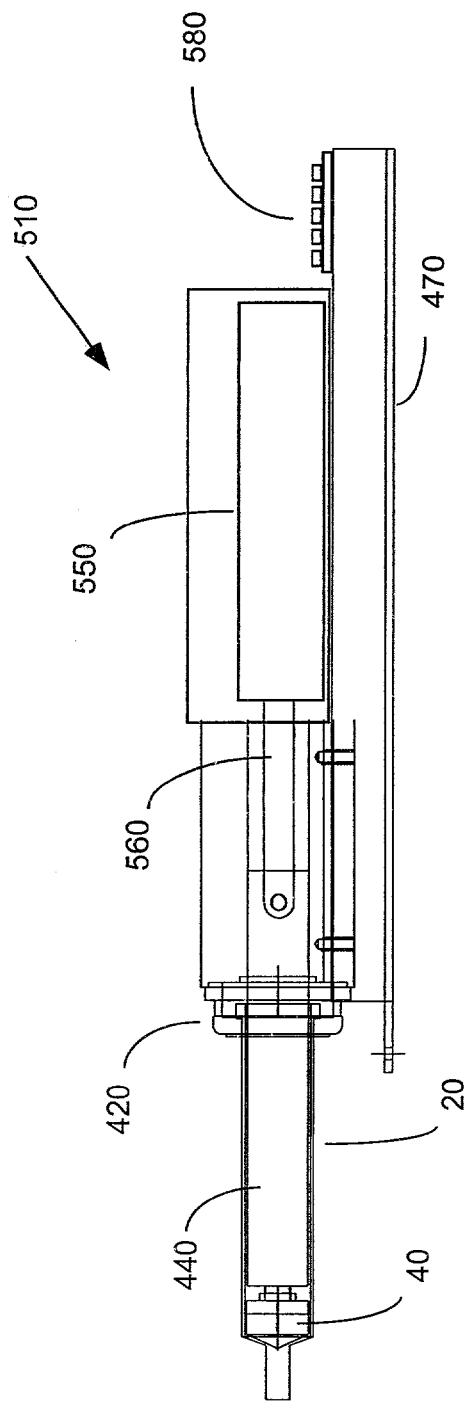
FIG. 4C illustrates a side, cross-sectional view of a syringe loader of the present invention including powered plunger extension.

FIG. 4C illustrates an off-injector syringe loader 510, similar in operation to syringe loader 410. However, lever arm 450 of syringe loader 410 is replaced by a powered drive mechanism 550, such as a screw drive. Powered screw drive 550 is operatively connected to plunger extension 440 via a connecting member 560. Drive screw 550 and thereby plunger extension 440 and plunger 40 can, for example, be controlled via a control pad 580. Because syringe loader 510 preferably is not used to inject fluid into a patient, but only to load injection fluid into syringe 20, any control circuitry/software used to operate drive screw 550 can be much less complicated and costly than similar control circuitry/software required in, for example, a powered injector such as injector 10 or injector 114.

Figure 4D:
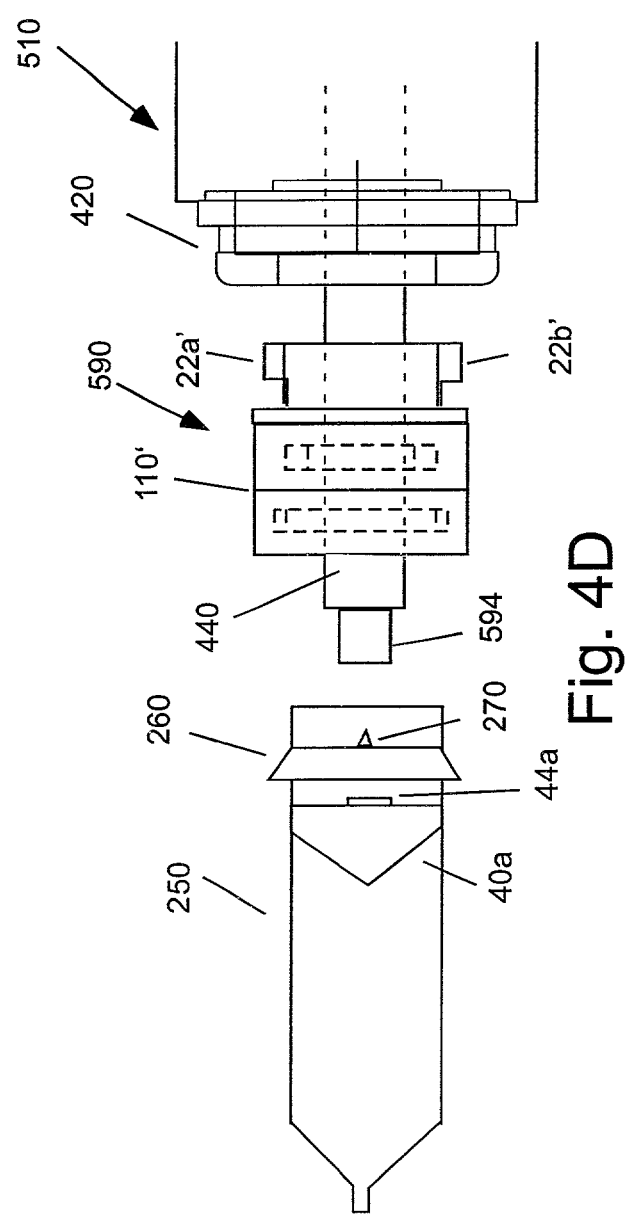
FIG. 4D illustrates the syringe loader of FIG. 4C with a syringe adapter and a plunger adapter for use of an alternative syringe with the syringe loader.

FIG. 4D illustrates use of an adapter 590 including a forward portion 110' that operates in generally the same manner as releasable mounting mechanism 110 described above to attach syringe 250 thereto. A rearward portion of adapter 590 includes flanges 22a' and 22b' to attach adapter 590 to syringe mount 420 of syringe loader 410 or 510, thereby adapting syringe 250 for use with syringe loader 410 or 510. In the case that capture member 44a of plunger 40a differs from L-shaped capture members 42 and 44 described above, a plunger adapter 594 can be used to connect plunger extension 440 to plunger 40a of syringe 250.

Figure 4E:
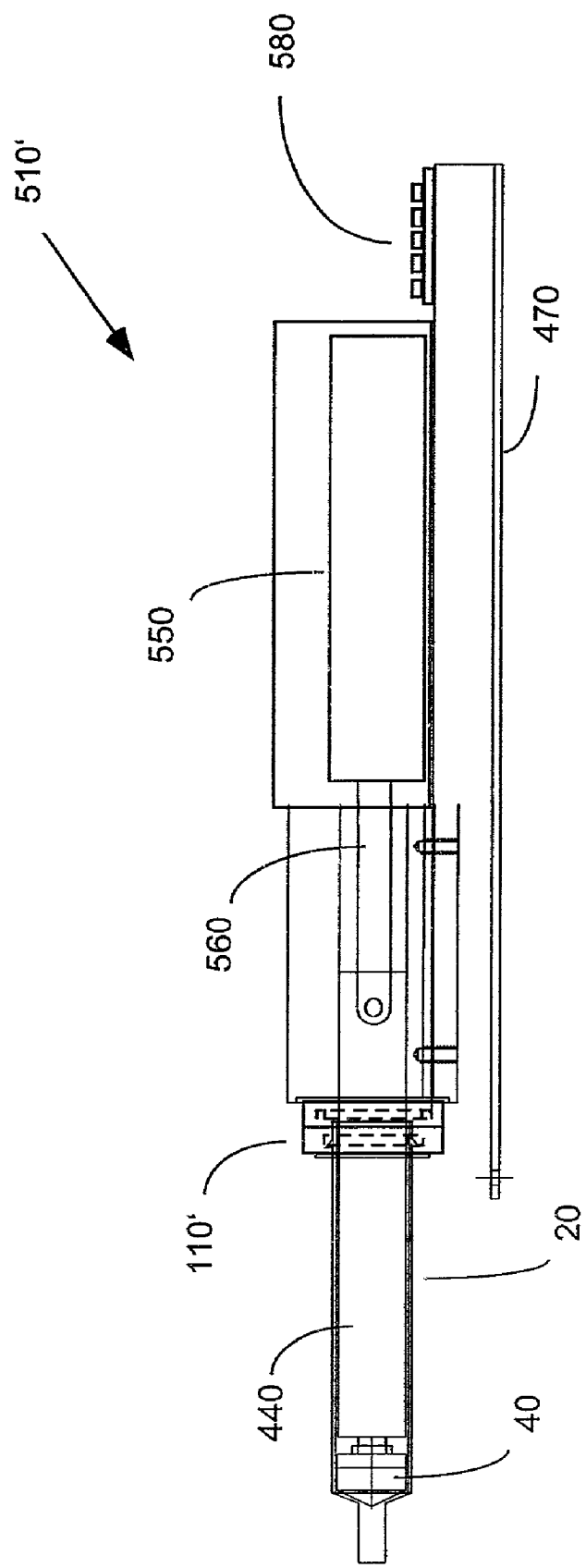
FIG. 4E illustrates the syringe loader of FIG. 4C with a different syringe mount for use of the syringe loader with an alternative syringe.

As illustrated in FIG. 4E, syringe mount 420 can also be replaced with syringe mounting mechanism 110' to connect syringe 250 directly to syringe loader 510' without use of an adapter. As clear to one skilled in the art, many other sizes and/or types of syringes can be accommodated by the syringe loaders of the present invention by use of corresponding syringe mounts or adapters. A syringe mounting mechanism of the syringe loaders of the present invention can easily be made removable (using, for example, cooperating slots and flanges) to facilitate use of different syringe mounts for different syringes. Moreover, more than one syringe mount can be included in a single syringe mounting mechanism, which can, for example, be slidable or rotatable to bring the appropriate syringe mount for a particular syringe into operation.

FIGS. 5A through 5I illustrate another embodiment of an off-injector syringe loader 610 of the present invention. Syringe loader 610 includes a syringe mount or syringe interface 700 that operates similar to the manner of the mounting mechanism of interface 60 of injector 10 as well as syringe mounts 320 and 420. However, syringe interface 700, which is discussed in further detail below, is suitable to attach syringes of different size to syringe loader 610 without the use of any adapter(s) and without user manipulation/ adjustment of the mechanics of syringe loader 610.

Syringe loader 610 includes an outer housing 620 and a support frame 630 housed within housing 620. In one embodiment, housing 630 was fabricated from TEFLON- impregnated aluminum. A plunger extension 640 adapted to impart motion to, for example, plunger 40 (as described above), is slidably disposed within support frame 630 of syringe loader 610 to pass through a passage 720 in syringe mount 700. Plunger extension 640 is in operative connection with a lever arm 650 via, for example, a pin 660. Lever arm 650 is rotatable to advance or retract plunger extension 640 via a dual slot arrangement as illustrated, for example, in FIGS. 5B and 5F. In that regard, lever arm 650 is attached to a pin 670 at a forward end thereof. As lever arm 650 is rotated (via, for example, application of force to handle 652) in a forward direction from its rearward position (see, for example, FIGS. 5F and 5I) to advance plunger extension 640, pin 670 travels downward (in the orientation of, for example, FIGS. 5B and 5F) within a slot 632 formed in support frame 630, and pin 660 travels forward within slot 634 formed within support frame 630. The motion of pins 660 and 670 within slots 634 and 632, respectively, and the motion of lever arm 650 are represented by arrows in FIG. 5F. Lever arm 650 provides mechanical advantage for ease of operation. Using the dual slot linkage arrangement of syringe loader 610, the stroke of the lever arm can be reduced as compared to the linkage assemblies used in syringe loaders 410 and 510 while providing similar mechanical advantage. During rotation, lever arm 650 travels through upper slots 638 and 628 formed in support frame 630 and housing 620, respectively.

Similar to syringe loader 410, syringe loader 610 preferably includes a base or mounting plate 680, which is preferably attachable to a surface (for example, a counter top or a wall) via any suitable attachment means. FIG. 5G illustrates one embodiment of a sequence of steps carried out to mount syringe loader 610 to a wall as follows:
1. Mounting plate 680 is preferably positioned in a desired location (for example, near the entrance outside of or within an MR room) such that top/forward mounting hole 682a is preferably between approximately 49 inches and approximately 53 inches from the floor to facilitate use by personnel of different heights. When mounting upon a wall of stud construction, mounting holes 682a and 682b are preferably positioned over a stud.
2. While maintaining mounting plate 680 in a generally vertical position, the locations of mounting holes 682a and 682b can be marked.
3. Pilot holes can then be drilled into the mounting surface at the marked locations for anchorage of suitable mounting hardware for mounting plate 680 as known in the art (for example, 2¼ inch tap con screws for wood studs and masonry, or hollow wall anchors for metal studs and drywall).
4. Mounting plate 680 is then affixed to the wall via mounting holes 682a and 682b.
5. After attachment of mounting plate 680 to the wall, support frame 630 is connected to mounting plate 680. In one embodiment (as illustrated in FIGS. 5A thorough 5G), support frame 630 is slid onto mounting plate 680 until a slot 683 formed in a base flange 636 of support member 630 is fully seated onto an alignment stud 684 projecting from base plate 680.
6. In this embodiment, support frame 630 is then rotated until generally aligned with mounting plate 680, with lever arm 650 at the bottom (in the orientation of FIG. 5G).
7. At this point, thumb screws 684a and 684b positioned at the top/rear of support frame 630 are tightened to secure support frame 630 to mounting plate 680. Thumbscrews 684a and 684b can be spring loaded using, for example, springs 685a and 685b.
8. Housing 620 is then slid onto support frame 630 until it is fully seated as shown in FIG. 5G.
9. Thumbscrews 622a and 622b positioned at the bottom/ front of the housing 620 are then tightened to secure housing 620 to mounting plate 680. Thumbscrews 622a and 622b can be spring loaded using, for example, springs 624a and 624b.

As described above, adapters can be used to attach different types and/or sizes of syringes to the syringe loaders of the present invention. However, attachment of adapters can use valuable operator time and storage/retrieval of multiple types of adapters can be a problem. Alternatively, a syringe mount or interface that is suitable to attach more than one size of syringe thereto can be provided. Such syringe interfaces are described in U.S. Provisional Patent Application Ser. No. 60/317,255, filed on Sep. 5, 2001, assigned to the assignee of the present invention, the disclosure of which is incorporated herein by reference.

In general, such syringe interfaces include a plurality of syringe mount apertures having different dimensions to attach each of a plurality of syringes (equipped with mounting flanges) to the syringe interface. In that regard, each of the plurality of syringes has a different mounting flange dimension. Each of the plurality of syringe mount apertures is in general alignment with the axis of the plunger extension of the syringe loader (or other drive member).

Syringe 20 can, for example, be removably connected to syringe interface 700 generally as described in U.S. Pat. No. 5,383,858. In that regard, as best shown in FIG. 5E, syringe interface 700 can include a first mount or mount aperture 710 having a first opening 720 formed therein. Plunger extension 640 is reciprocally mounted within syringe loader 610 and is extendible through opening 720. Mount 710 includes receiving slots 722a and 722b, which are preferably positioned opposite one another around opening 720. Receiving flanges 724a and 724b are preferably positioned opposite one another and between receiving slots 722a and 722b and extend inwardly into opening 720.

To attach syringe 20 to syringe loader 610 (see FIG. 5C), the rearward end of syringe 20 is inserted into interface 700 (and first mount 710) such that mounting flanges 22a and 22b are inserted into receiving slots 722a and 722b, respectively. In one embodiment, flange 644 of plunger extension 640 preferably simultaneously aligns with and engages capture members 42 and 44 of syringe plunger 40 (as described above) when mounting flanges 22a and 22b are aligned with slots 722a and 722b.

Once mounting flanges 22a and 22b are inserted into receiving slots 722a and 722b, respectively, and plunger extension 640 is in position to be received by the syringe plunger, the operator rotates syringe 20 approximately 90 degrees such that mounting flanges 22a and 22b move behind and are engaged by receiving flanges 724a and 724b, respectively, and syringe plunger 40 is engaged by plunger extension 640. Syringe interface 700 may include one or more stop mechanisms such as, for example, abutment member 726a extending, for example, from at least one of the retaining flanges 724a and 724b, to prevent rotation of syringe 20 more than 90 degrees. Tactile, visual or audible feedback can be provided to the operator via, for example, cooperating members (not shown) on syringe 20 and syringe interface 700 to inform the operator that secure connection has been achieved. After securely attaching syringe 20 to syringe interface 700 (and thereby to syringe loader 610), advancing plunger extension 640 in a forward direction will apply a motive force to syringe plunger 40 to advance syringe plunger 40 forward within syringe 20, thereby forcing the contents of syringe 20 out of syringe tip 26. Retracting plunger extension 640 in a rearward direction will cause the syringe plunger to move rearward within syringe 20, thereby drawing fluid into syringe 20.

As best shown in FIGS. 5E and 5C, syringe interface 700 also includes at least a second mount or mount aperture 810 having an opening 820 formed therein that is larger than opening 720 and has generally the same center as opening 720. Plunger extension 640 is thus also extendible through opening 820 to cooperate with syringe plunger 40 as described above. Mount 810 includes receiving slots (only 822a is shown), which are preferably positioned opposite one another around opening 820. Retaining flanges 824a and 824b are preferably positioned opposite one another and between receiving slots 822a and 822b and extend inwardly into opening 820.

To attach a syringe 20' to syringe loader 610 (as shown in FIG. 5D), the rearward end of syringe 20' is inserted into injector opening 820 such that mounting flanges 22a' and 22b' are inserted into receiving slots 822a and 822b, respectively. The diameter/volume of syringe 20' is greater than the diameter of syringe 20. As syringe 20' is moved rearward, it contacts mount 710. Mount 710 is preferably movable (for example, slidable in an axial direction) such that mount 710 moves rearward when contacted by syringe 20'. Axial rearward movement of mount 710 allows syringe 20' to move rearward and, subsequently, to be rotated relative to mount 810 so that flanges 22a' and 22b' of syringe 20' are rotated into engagement with (i.e., behind) retaining flanges 824a and 824b, as described above for syringe 20 and retaining flanges 724a and 724b.

In one embodiment, mount 710 is attached to or formed integrally with a plate 850 that is slidably mounted on posts 860a and 860b via holes or passages 852a and 852b, respectively, formed in plate 850. Preferably, mount 710 is biased in a forward position as illustrated, for example, in FIG. 5C. In the embodiment of FIGS. 5A through 5I, springs 870a and 870b are positioned on posts 860a and 860b to bias mount 710 in a forward position. Springs 870a and 870b are retained on posts 860a and 860b by plate 850 and abutment elements 862a and 862b (see FIG. 5E) positioned on a rearward end of posts 860a and 860b, respectively.

Other syringe interfaces for attachment of syringes of various sizes are suitable for use in the present invention. As described in U.S. Provisional Patent Application Ser. No. 60/317,255, filed on Sep. 5, 2001, a syringe interface 890a (see FIG. 5H) suitable for use with the syringe loaders of the present invention can also include a plurality of syringe mounts 890aa, 890ab and 890ac that are fixed at different axial positions. Moreover, a syringe interface 890b can include a generally cone-shaped or frustum-shaped threaded flange 890ba to cooperate with a corresponding threaded flange on each of a plurality of syringes (each syringe size having a frustum-shaped threaded flange of a different diameter). The radius of threaded flange 890ba decreases as one moves rearward within the syringe interface. A syringe interface 890c can also include one or more retention members that are movable to adjust the radial position of retaining flanges formed on a radially inward end thereof to cooperate with and retain each of a plurality of syringes. For example, each retention member 890ca of the syringe interface 890c can be rotatable in a plane generally parallel to an axis of the syringe to adjust the radial position of retaining flanges 890cb. Alternatively, each retention member 890da of a syringe interface 890d can alternatively be rotatable in a plane generally parallel to the radius of the syringe to adjust the radial position of retaining flanges 890db.

An example of the use of syringe loader 610 with a 65 ml syringe sold by Medrad, Inc, for use with its Spectris® MR injector is illustrated generally in FIG. 5I. In this example, the following steps are carried out:

1. First, unused, empty syringe 20 (or 20') is inserted into syringe interface 700 such that the drip flange 28 of syringe 20 is at the bottom/rear, and the graduations (if any) of syringe 20 are facing right. (When loading syringe 20', mount 710 moves down/rearward as described above.)
2. Syringe 20 is then rotated clockwise until it stops (approximately ¼ turn or 90°). The graduations on syringe 20 will now be facing forward.
3. Handle 652 of lever arm 650 is then rotated upward/forward until it stops, thereby advancing plunger 40 to its forward position within syringe 20.
4. Using an appropriate spike/connector, a saline, contrast medium or other injection fluid container 895 is connected to the tip 26 of syringe 20 (preferably using good sterile technique).
5. Handle 652 of lever arm 650 is then pulled downward/rearward until the desired amount of saline or contrast medium has entered syringe 20.
6. Container 895 is then disconnected from syringe 20.
7. Handle 652 of lever arm 650 is then preferably pulled fully downward/rearward until it stops.

8. Syringe 20 is rotated counterclockwise until it stops (approximately ¼ turn or 90°). (Syringe 20' may be pushed upward/forward upon disconnection as a result of the forward bias of plate 850).
9. Loaded syringe 20 may then be withdrawn from syringe loader 610.

At this point, syringe 20 can be capped (for example, with a cap/connector tube) using good sterile technique. Syringe 20 is preferably labeled to identify loaded medium.

Figure 5F:
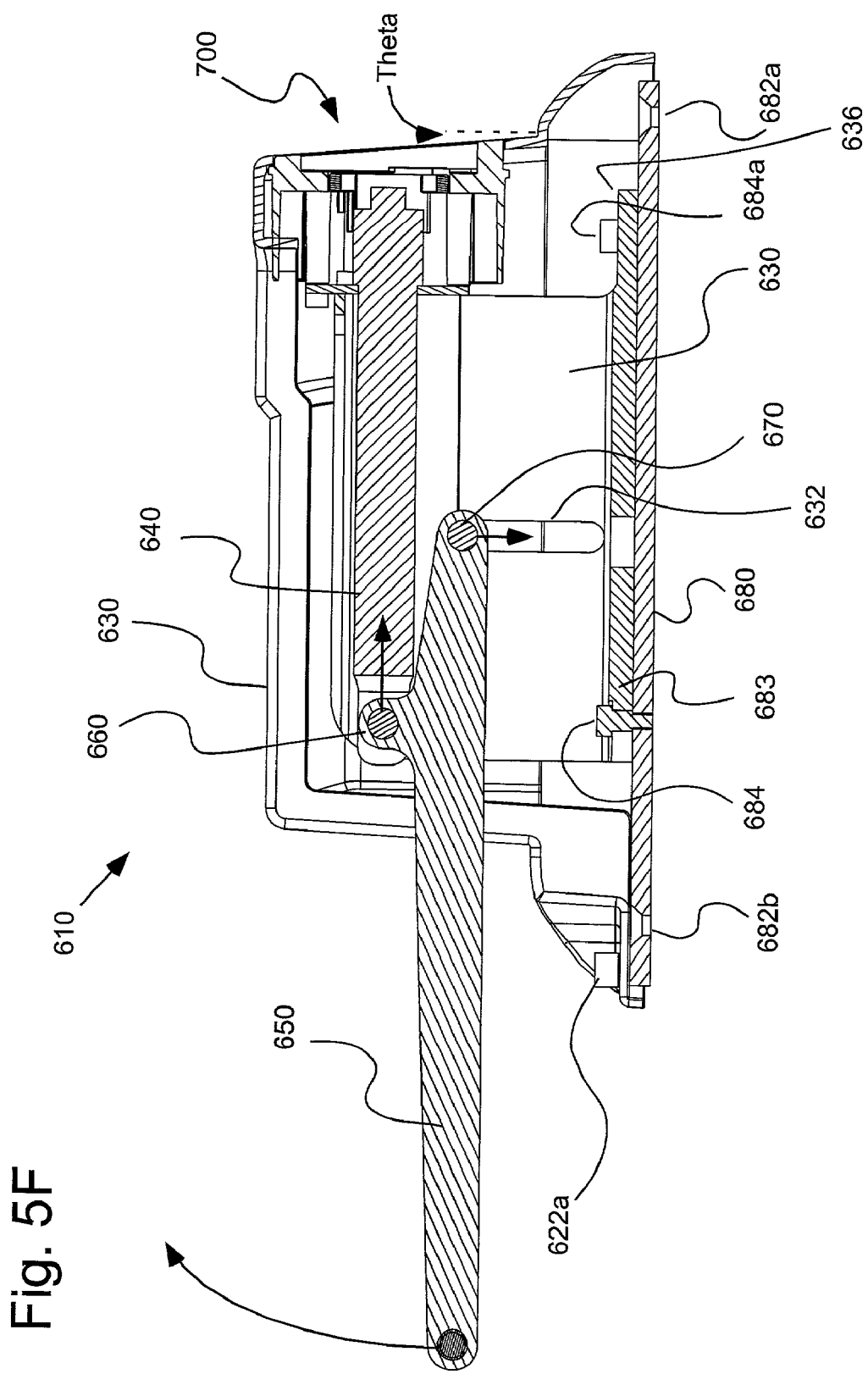
FIG. 5F illustrates a side, cross-sectional view of the syringe loader of FIG. 5A.
Figure 5G:
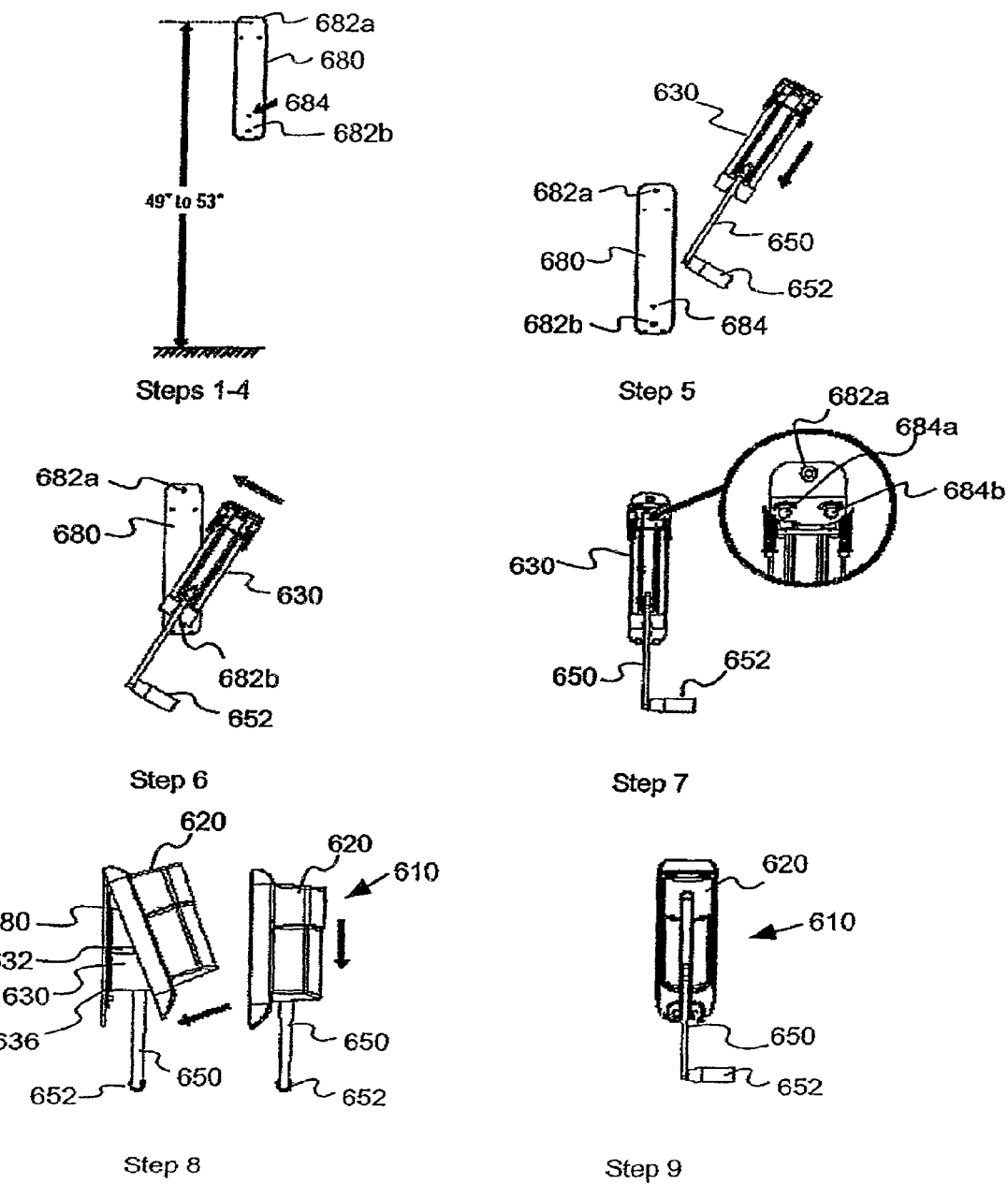
FIG. 5G illustrates one embodiment of a process for mounting the syringe loader of FIG. 5A (in which the view of all steps other than step 8 is a top view; step 8 illustrates a side view)
Figure 5H:
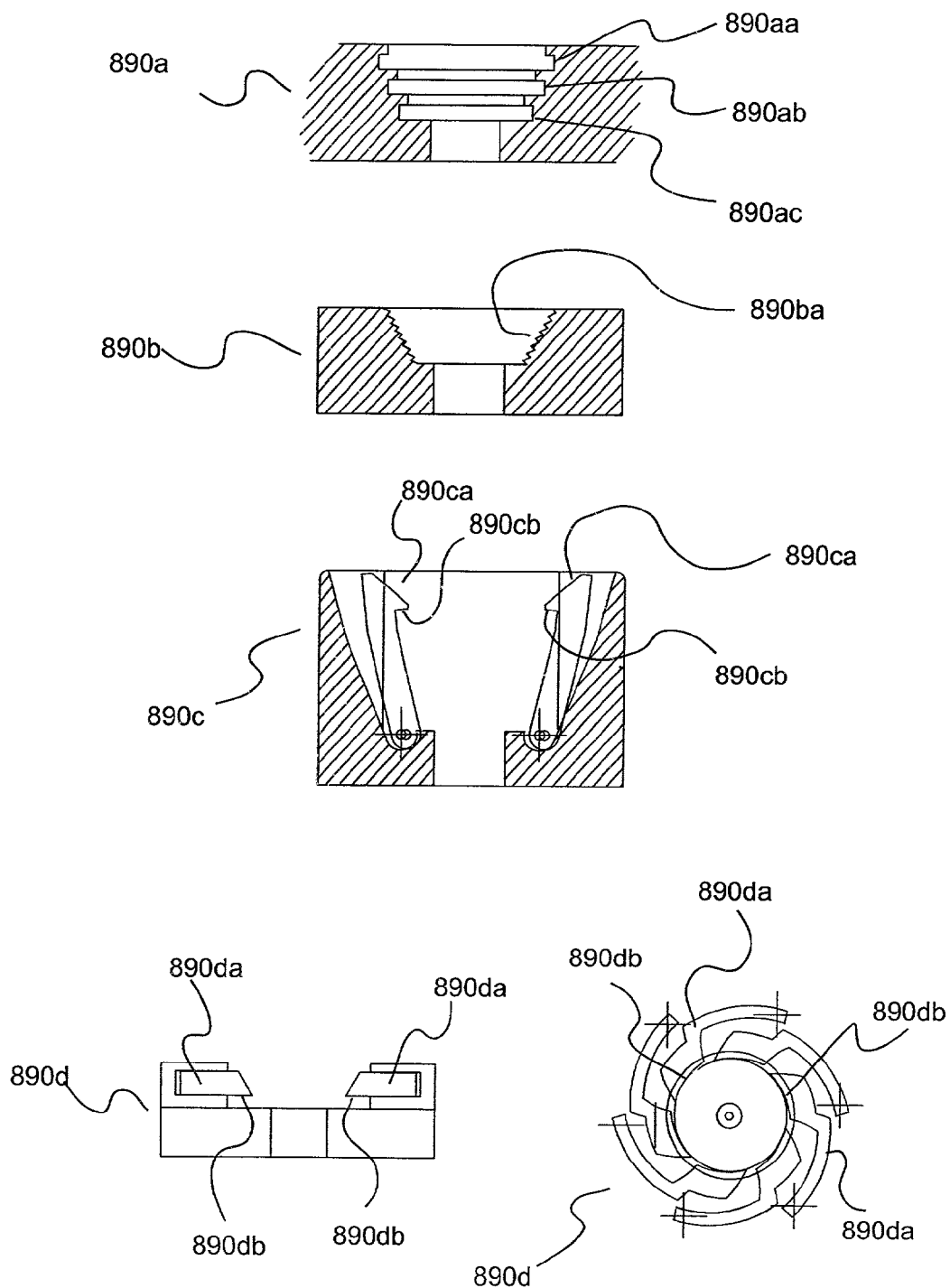
FIG. 5H illustrates several alternative embodiments of syringe interfaces suitable for use with the syringe loaders of the present invention.
Figure 51:
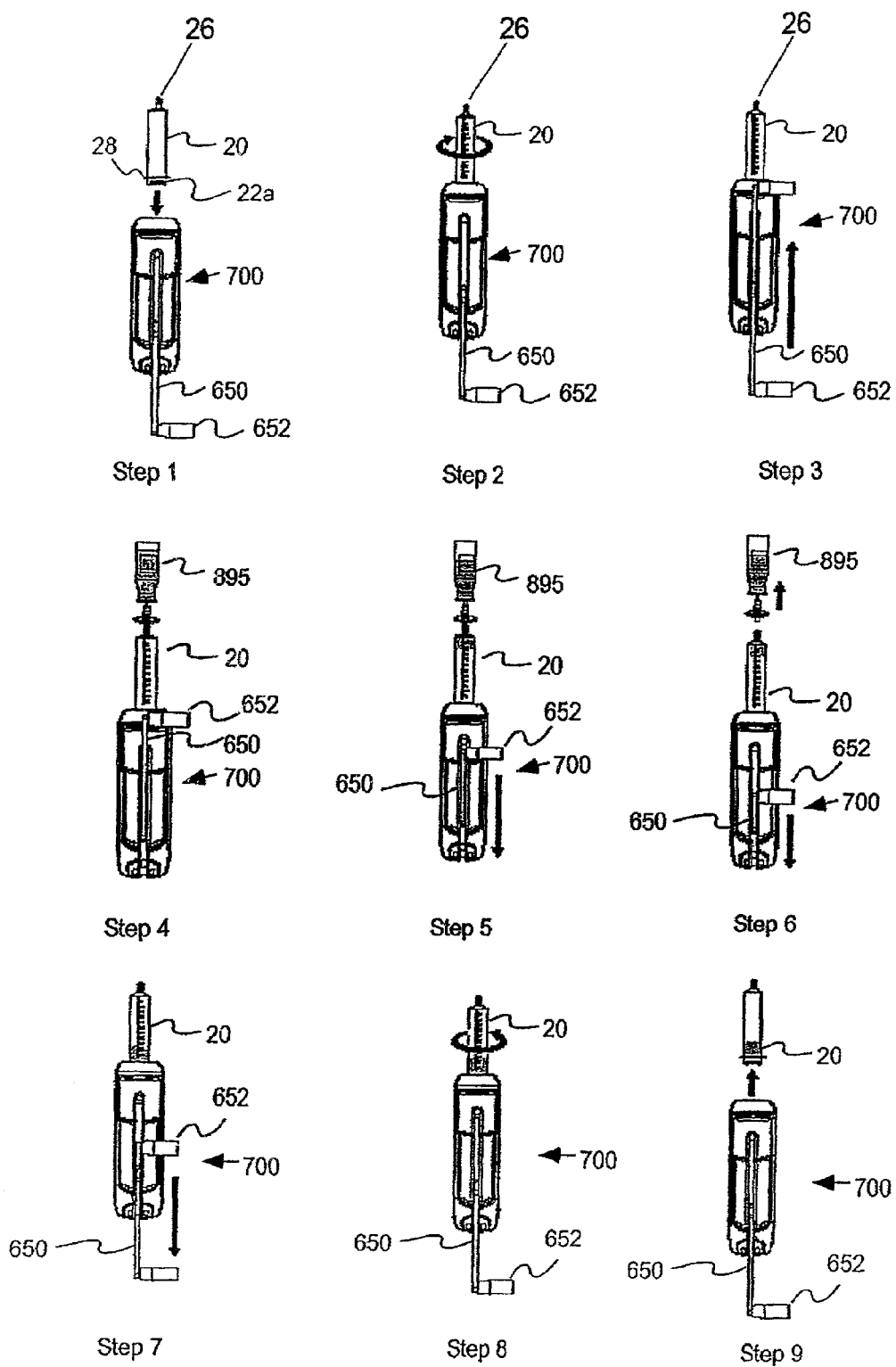

As best illustrated in, for example, FIG. 5F, a front face of syringe loader 610 and of syringe interface 700 can be angled at an angle Theta or θ from the vertical to facilitate runoff of spilled or leaked contrast (and/or other injection media) during a loading procedure as described above in connection with FIG. 5I (particularly when the syringe loader is mounted vertically on a wall). Spillage or leakage during loading of syringes is a common occurrence. Indeed, the syringe loaders of the present invention provide the benefit of eliminating the use of injectors to load empty syringes. Contrast media and other injection fluids can damage the internal components of powered injectors. Although to a much lesser extent, buildup of such injection fluids can also be detrimental to the syringe loaders of the present invention.

Figure 6A:
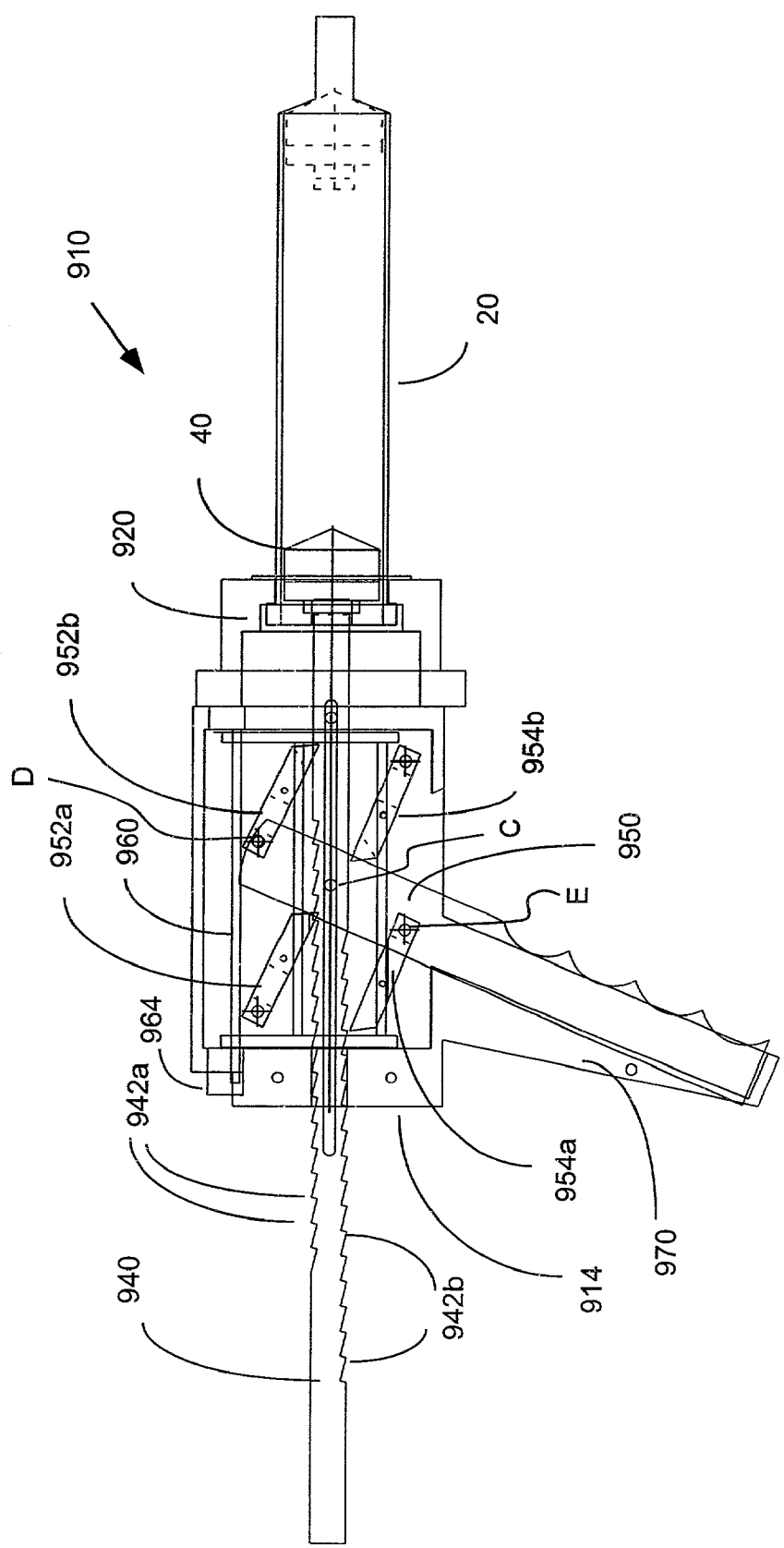
FIG. 6A illustrates a side, cross-sectional view of another embodiment of a syringe loader of the present invention in which the syringe loader is set up to advance the plunger.

FIGS. 6A and 6B illustrate another embodiment of an off-injector syringe loader 910. Syringe loader 910 includes a syringe mount 920 as described above. Syringe loader 910 also includes a plunger extension 940 that operates to impart motion to plunger 40. In this embodiment, plunger extension 940 includes ratchet teeth 942a on an upper side thereof and ratchet teeth 942b on a lower side thereof. Upper pawls 952a and 952b cooperate with upper ratchet teeth 942a to impart forward motion to plunger extension 940. Lower pawls 954a and 954b cooperate with lower ratchet teeth 942b to impart rearward motion to plunger extension 940. In that regard, a rotating grip handle 950 rotates about a point C within housing 914 of syringe loader 910. Pawl 952b is rotatably attached to handle 950 at a point D on a first side of (for example, in the orientation of FIG. 6A, above) point C, while pawl 954a is rotatably attached to handle 950 at a point E on a second side of (for example, in the orientation of FIG. 6A, below) point C.

The position of a carriage 960 is vertically adjustable (using, for example, an adjustment knob 964) to a first position (illustrated in FIG. 6A) to bring upper pawls 952a and 952b into operative connection with plunger extension 940 or to a second position (illustrated in the lower portion of FIG. 6B) to bring lower pawls 954a and 954b into operative connection with plunger extension 940. Pawls 952a, 952b, 954a and 954b are preferably biased towards an engagement position (using, for example springs) as known in the mechanical arts unless prevented therefrom by carriage 960. Pawls 952a and 954b preferably are not provided motive force by rotation of handle 950, but are present to help ensure that plunger extension 940 does not move in a direction other than as determined by the position of carriage 960.

FIG. 6B illustrates the use of rotating handle 950 to expel and load injection fluid into a syringe. Depending on the position of carriage 960, the same pumping, gripping motion can either advance plunger extension 940 or retract plunger extension 940, as illustrated in FIG. 6B. Syringe loader 910 includes a stationary grip handle 970 that is gripped by the thumb of the users hand. During use of syringe loader 910, the user grips rotating handle 950 with the finger tips of the same hand and either advances or retracts plunger 40 (depending on the position of carriage 960) by alternatively closing and opening and gripping handle 950, similar to the motion used with common caulking guns. Rotating handle 950 is preferably biased in an "open" position (using, for example a spring (not shown)) with the lower end thereof rotated away from stationary handle 970, as illustrated in the left-hand portion of FIG. 6B.

Figure 7A:
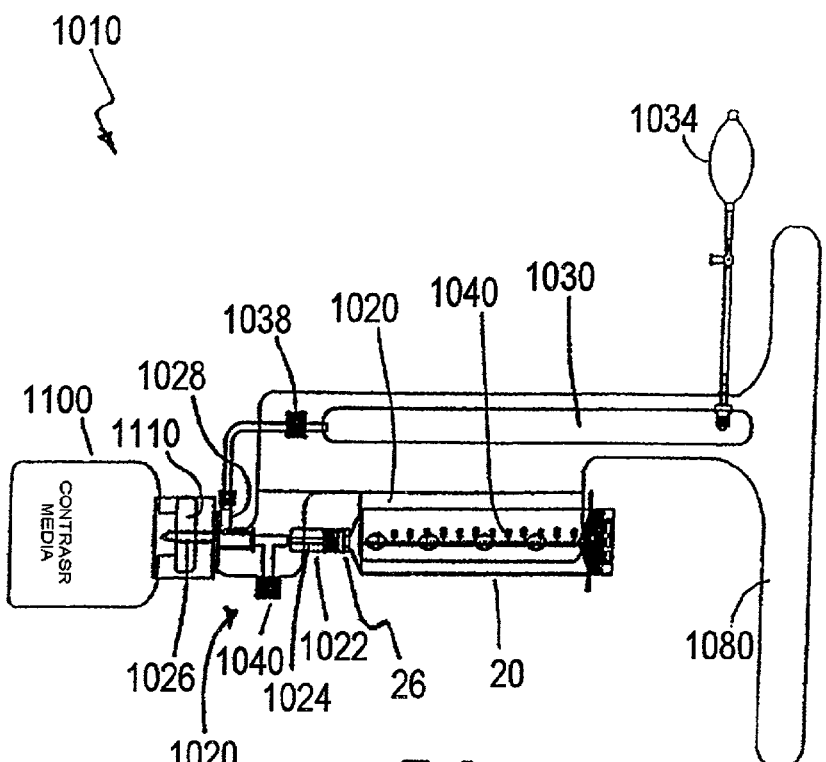
FIG. 7A illustrates a front view of another embodiment of a syringe loader of the present invention in which the syringe loader is wall-mountable.
Figure 7B:
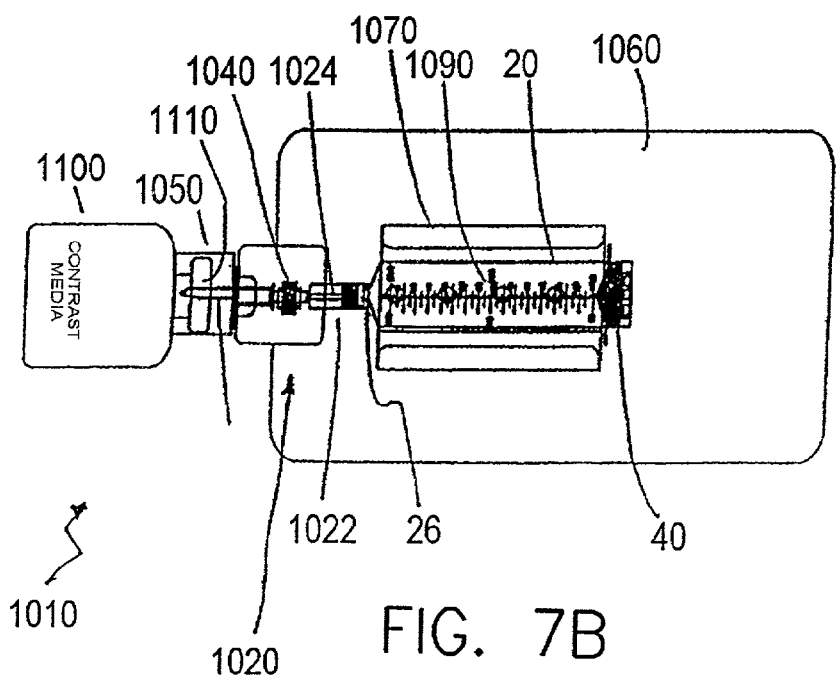
FIG. 7B illustrates a side view of an embodiment of a syringe loader similar in operation to the syringe loader of FIG. 7A except that the syringe loader includes a stand to support the syringe loader on a surface.
Figure 7C:
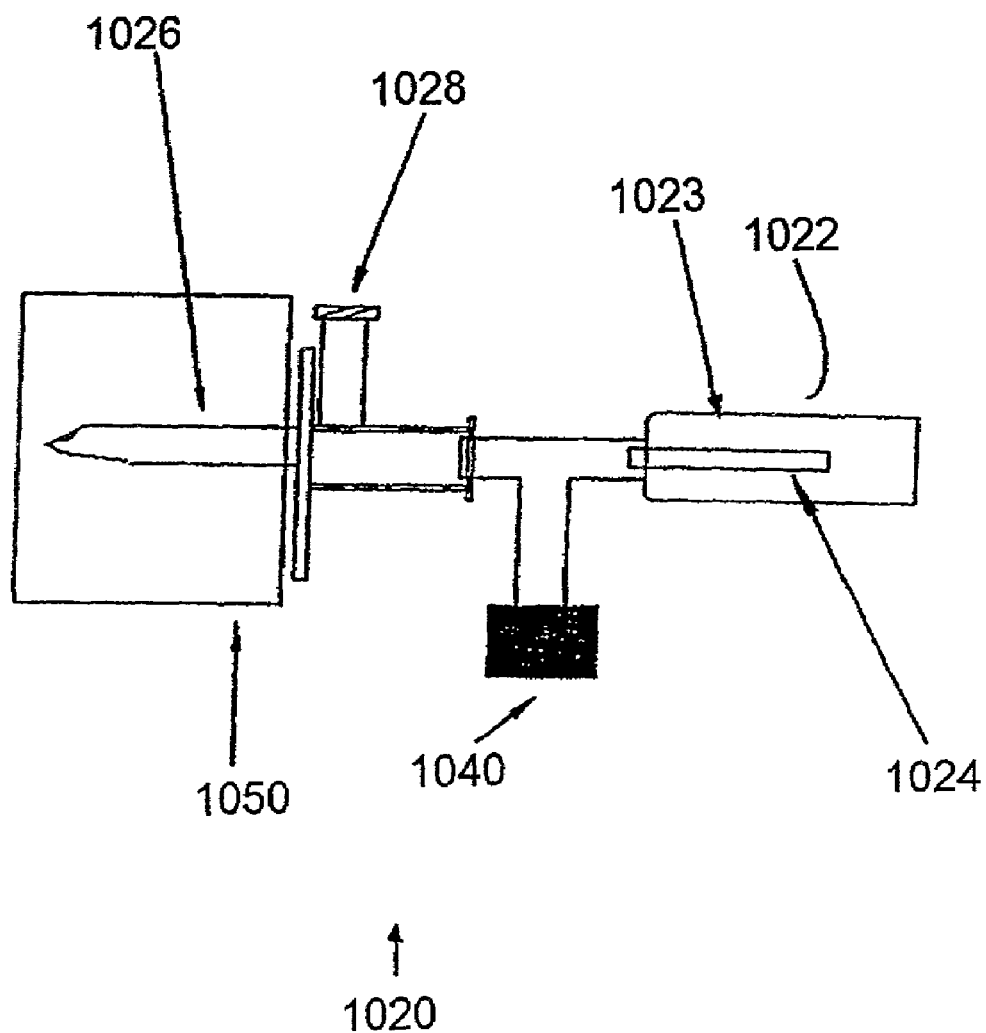
FIG. 7C illustrates a side view of the connector of the syringe loaders of FIGS. 7A and 7B.

FIGS. 7A through 7C illustrate an embodiment of an off-injector syringe loader in which gas pressure is used to force injection fluid into syringe 20. In this embodiment, syringe loader 1010 does not attach to a rear mounting mechanism of a syringe (for example, flanges 22a and 22b of syringe 20) as described above for syringe loaders 310, 410, 510, 510', 610 and 910. Instead, syringe loader 1010 includes a connector 1020 that connects a source of injection fluid (for example, contrast media bottle 1100) with syringe 20. Connector 1020 includes a connection mechanism 1022 on one end thereof to connect to syringe tip 26. Connection mechanism 1022 can, for example, include a luer connection as known in the medical arts. Conduit or passage 1024 of connector 1020 is brought into fluid connection with the interior of syringe 20 when connector 1020 is attached to, for example, syringe 20 or syringe 250. Connector 1020 is readily modifiable to attach to virtually any syringe design. A second connection mechanism 1026 is positioned on another end of connector 1020. In the embodiment of FIGS. 7A through 7C, connection mechanism 1026 includes a spike for connecting connector 1020 to contrast bottle 1100 which includes a septum 1110.

Connector 1020 includes a passage therethrough to place contrast bottle 1100 and syringe 20 in fluid connection when both are connected to connector 1020. Connector 1020 also includes an inlet 1028 to permit a pressurized gas to enter contrast bottle 1100. In one embodiment, pressurized air is used via connection of inlet 1028 to an air bladder 1030 that is in fluid connection with, for example, a ball pump 1034 to pressurize air. Preferably, a check valve 1038 is placed between air bladder 1030 and inlet 1028 to substantially prevent flow of air from inlet 1028 to air bladder 1030. Connector 1020 also preferably includes a valve such as a push valve 1040 that is closed during pressurization of contrast bottle 1100 via air bladder 1030 and ball pump 1034 to prevent air from passing into syringe 20. Once contrast bottle 1100 is sufficiently pressurized by pumping air therein, push valve 1040 is opened to allow pressurized contrast medium to flow into syringe 20 via conduit 1024.

Contrast bottle 1100 is preferably in a generally inverted position as illustrated in FIGS. 7A and 7B during the loading process to ensure that the pressurized gas (for example, air) rises to the bottom of contrast bottle 1100 and above the spike to prevent gas from passing into syringe 20. Moreover, the inverted orientation of contrast bottle 1100 allows gravity to assist in the filling of syringe 20. The top (that is, the opening) of inverted contrast bottle 1100 can, for example, rest within a generally cylindrical retainer or support 1050 provided on connector 1020 during the loading process.

Preferably, connection mechanism 1022 includes an outer portion 1023 that passes over syringe tip 26 during connection of connector 1020 to syringe 20. Conduit 1024 is preferably housed within outer portion 1023 such that conduit 1024 does not extend outside of (that is, beyond the lower edge of) outer portion 1023 to assist in preventing contaminants from contacting conduit 1024 (for example, during connection of connector 1020 to syringe 20), thereby assisting in maintaining the sterility of syringe 20.

In the embodiment of FIG. 7A, syringe loader 1010 is attached to a mounting base 1060 that is preferably adapted to mount syringe loader 1010 to a wall. A syringe retainer 1070 is attached to mounting base 1060 to retain syringe 20 during loading. In the embodiment of FIG. 7B, syringe loader 1020 is attached to a standing base unit 1080. Syringe retainer 1070 is attached to standing base unit 1080. Gradation members 1090 that are syringe dependent can be provided to assist in loading a desired amount of fluid into syringe 20.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. The scope of the invention is indicated by the following claims rather than by the foregoing description. All changes and variations that come within the meaning and range of equivalency of the claims are to be embraced within their scope.

What is claimed is:

1. A device for loading a fluid into a syringe comprising a body having a plunger slidably disposed therein and an attachment mechanism associated with the body for attaching the syringe to an injector comprising a mounting mechanism adapted to cooperate with the attachment mechanism on the syringe to mount the syringe on the injector, the device comprising:
   a syringe mounting mechanism adapted to cooperate with the attachment mechanism of the syringe to attach the syringe to the device;
   a drive member adapted to impart motion to the syringe plunger;
   a lever arm connected to the drive member to impart reciprocal linear motion to the syringe plunger; and
   a support frame defining a first slot and a second slot therein, the second slot being substantially perpendicular to the first slot, the lever arm being rotatably connected to the drive via a first pin positioned between the forward end and the rearward end of the lever arm and a second pin positioned forward of the first pin, the first pin traveling in the first slot and the second pin traveling in the second slot during rotation of the lever arm.

2. The device of claim 1 further comprising a mount that is attachable to a surface.

3. The device of claim 2 wherein the support frame is removably attachable to the mount.

4. A system comprising:
   a syringe comprising a syringe plunger;
   a powered injector to pressurize a fluid loaded into the syringe, the powered injector comprising a drive member to impart motion to the syringe plunger; and
   a syringe loader to load fluid into the syringe, the syringe loader comprising:
     a lever arm connected to the drive member to impart reciprocal linear motion to the syringe plunger; and
     a support frame defining a first slot and a second slot therein, the second slot being substantially perpendicular to the first slot, the lever arm being rotatably connected to the drive member via a first pin positioned between the forward end and the rearward end of the lever arm and a second pin positioned forward of the first pin, the first pin traveling in the first slot and the second pin traveling in the second slot during rotation of the lever arm.

5. The system of claim 4, further comprising a mount that is attachable to a surface.

6. The system of claim 5 wherein the support frame is removably attachable to the mount.

* * * * *

UNITED STATES PATENT AND TRADEMARK OFFICE
CERTIFICATE OF CORRECTION

PATENT NO. : 7,025,757 B2 Page 1 of 1
APPLICATION NO. : 10/067003
DATED : April 11, 2006
INVENTOR(S) : David M. Reilly, Frederick W. Trombley, III and Mark Trocki It is certified that error appears in the above-identified patent and that said Letters Patent is hereby corrected as shown below:

IN THE DRAWINGS:
In FIG. 7A, Sheet 22 of 23, in Box "1100", Line 1, delete "CONTRASR" and insert -- CONTRAST --, therefor.

IN THE SPECIFICATION:
In Column 1, Line 44, after "reference" insert -- . --.
In Column 4, Line 27, delete "DELIN®" and insert -- DELRIN® --, therefor.

IN THE CLAIMS:
In Column 16, Line 1, in Claim 1, after "drive" insert -- member --.
In Column 16, Line 7, in Claim 2, after "1" insert -- , --.

Signed and Sealed this

Twentieth Day of May, 2008

JON W. DUDAS
*Director of the United States Patent and Trademark Office*